United States Patent
Lee et al.

(10) Patent No.: US 11,933,754 B2
(45) Date of Patent: Mar. 19, 2024

(54) SENSOR AND METHOD FOR OPERATING SENSOR

(71) Applicant: LG ELECTRONICS INC., Seoul (KR)

(72) Inventors: Myungwon Lee, Seoul (KR); Daehyun Park, Seoul (KR); Hyunchul Kim, Seoul (KR); Soonyoung Min, Seoul (KR)

(73) Assignee: LG ELECTRONICS INC., Seoul (KR)

( * ) Notice: Subject to any disclaimer, the term of this patent is extended or adjusted under 35 U.S.C. 154(b) by 361 days.

(21) Appl. No.: 17/295,750

(22) PCT Filed: Dec. 6, 2019

(86) PCT No.: PCT/KR2019/017158
§ 371 (c)(1),
(2) Date: May 20, 2021

(87) PCT Pub. No.: WO2020/116979
PCT Pub. Date: Jun. 11, 2020

(65) Prior Publication Data
US 2022/0018796 A1     Jan. 20, 2022

Related U.S. Application Data

(60) Provisional application No. 62/776,382, filed on Dec. 6, 2018.

(51) Int. Cl.
| | | |
|---|---|---|
| G01N 27/22 | (2006.01) | |
| G01N 33/02 | (2006.01) | |
| H01Q 1/38 | (2006.01) | |
| H01Q 7/00 | (2006.01) | |
| H05K 1/09 | (2006.01) | |
| H05K 1/16 | (2006.01) | |

(52) U.S. Cl.
CPC .......... *G01N 27/228* (2013.01); *G01N 33/02* (2013.01); *H01Q 1/38* (2013.01); *H01Q 7/00* (2013.01);
(Continued)

(58) Field of Classification Search
CPC ...... G01N 27/228; G01N 33/02; G01N 27/02; G01N 27/30; G01N 27/416; H01Q 1/38;
(Continued)

(56) References Cited

U.S. PATENT DOCUMENTS

| | | | |
|---|---|---|---|
| 2009/0218238 A1 | 9/2009 | Dasgupta et al. | |
| 2009/0267617 A1* | 10/2009 | Seyfi | G01N 27/023 |
| | | | 324/655 |

(Continued)

FOREIGN PATENT DOCUMENTS

| | | |
|---|---|---|
| KR | 10-2008-0097011 A | 11/2008 |
| KR | 10-2015-0080224 A | 7/2015 |

(Continued)

*Primary Examiner* — Akm Zakaria
(74) *Attorney, Agent, or Firm* — Birch, Stewart, Kolasch & Birch, LLP

(57) ABSTRACT

The present invention provides a sensor comprising: a substrate; an antenna pattern formed in a spiral shape on the substrate; first and second electrodes formed on the substrate and spaced apart from each other in parallel; a circuit wiring formed to be connected to each of the first and second electrodes; and an element bonded to the antenna pattern and the circuit wiring, wherein cross sections of the first and second electrodes have a curvature.

39 Claims, 16 Drawing Sheets

(52) U.S. Cl.
CPC ............... *H05K 1/092* (2013.01); *H05K 1/16* (2013.01); *H05K 2201/10098* (2013.01)

(58) Field of Classification Search
CPC ............ H01Q 7/00; H05K 1/092; H05K 1/16; H05K 2201/10098; H05K 1/095; H05K 1/11; H05K 1/165; H05K 2201/0245; H05K 2201/098; H05K 2201/10151
See application file for complete search history.

(56) References Cited

U.S. PATENT DOCUMENTS

| | | | |
|---|---|---|---|
| 2010/0155288 A1* | 6/2010 | Harper | B32B 15/08 428/479.3 |
| 2015/0309638 A1* | 10/2015 | Lin | G06F 3/0443 345/174 |
| 2016/0050750 A1* | 2/2016 | Rogers | H05K 3/285 361/767 |
| 2016/0116429 A1* | 4/2016 | Murase | G01N 27/301 174/251 |
| 2017/0234894 A1* | 8/2017 | LaBelle | G01N 27/327 435/7.4 |
| 2017/0307453 A1* | 10/2017 | Cotton | G01M 5/0083 |
| 2018/0206321 A1* | 7/2018 | Morfill | H05H 1/2439 |
| 2019/0331623 A1 | 10/2019 | Kim et al. | |
| 2020/0110049 A1* | 4/2020 | Lee | G01N 33/02 |

FOREIGN PATENT DOCUMENTS

| | | |
|---|---|---|
| KR | 10-1590531 B1 | 2/2016 |
| KR | 10-1681236 B1 | 11/2016 |
| KR | 10-2018-0082949 A | 7/2018 |

* cited by examiner

SENSOR AND METHOD FOR OPERATING SENSOR

CROSS REFERENCE TO RELATED APPLICATIONS

This application is the National Phase of PCT/KR2019/017158 filed on Dec. 6, 2019, which claims priority under 35 U.S.C. § 119(e) to U.S. Provisional Application No. 62/776,382 filed on Dec. 6, 2018, all of these applications are hereby expressly incorporated by reference into the present application.

TECHNICAL FIELD

The present disclosure relates to a sensor and a method for operating the sensor that facilitates measuring salinity and water quality of a sensing target material.

BACKGROUND ART

Due to a recent change in diet, number of adult diseases such as hypertension, hyperlipidemia, and diabetes has increased rapidly, which has become a social issue. However, in most cases, the diseases are often found in a state that has progressed to a certain level, and thus social costs (costs for health examination and medical treatment) are increasing. Also, in order to prevent adult diseases, public's interest in food safety and in safety of residual pesticides in vegetables and fruits is increasing.

However, it costs a lot and is inconvenient when it comes to individually inspecting various detection information such as food safety. In addition, it is very inconvenient and difficult to comprehensively and continuously manage food safety.

In the related art, a terminal-type sensor has been used to check salinity or sugar content of food, or degeneration of fat and oil. The terminal-type sensor has an advantage of individually checking salinity of food to provide a result of the check to a user. Meanwhile, the terminal-type sensor has several disadvantages as follows.

First, since the terminal-type sensor requires a separate power source or battery for operation, the terminal-type sensor cannot operate in an environment where it is difficult to supply power.

In addition, the terminal-type sensor is difficult to be popularized because a unit price of the product is relatively high.

Finally, it is inconvenient to carry the terminal-type sensor.

Therefore, there is a need to develop a sensor that can solve the disadvantages of the terminal-type sensor.

DETAILED DESCRIPTION OF THE DISCLOSURE

Technical Problem

An aspect of the present disclosure is to provide a sensor and a method for operating the sensor capable of measuring salinity and water quality of a sensing target material.

In addition, an aspect of the present disclosure to provide a sensor and a method for operating the sensor capable of suppressing oxidation and corrosion of a sensing electrode when measuring salinity and water quality of a sensing target material.

In addition, an aspect of the present disclosure is to provide a sensor and a method for operating the sensor capable of measuring salinity and water quality of a sensing target material using direct current power generated by harvesting energy from a radio signal received from an external device.

In addition, an aspect of the present disclosure is to provide a sensor and a method for operating the sensor that generates direct current power by harvesting energy from a radio signal received from an external device to transmit a digital signal corresponding to a result of measuring salinity and water quality of a sensing target material to the external device, and has an enhanced portability.

However, aspects of the present disclosure are not limited to the above aspects, and other aspects that are not mentioned will be clearly understood with the following description.

Technical Solution

A sensor according to a first embodiment of the present disclosure may include a substrate, an antenna pattern formed in a spiral shape on the substrate, a first electrode and a second electrode formed on the substrate and spaced apart from each other in parallel, a circuit wiring formed to be connected to each of the first electrode and the second electrode, and an element bonded to the antenna pattern and the circuit wiring, wherein cross sections of the first electrode and the second electrode each may have a curvature.

The first electrode and the second electrode each may form an acute contact angle with the substrate, the first electrode and the second electrode each may have a width of 50 µm to 200 µm, a distance between the first electrode and the second electrode may be from 900 µm to 1,500 µm, and a thickness of each of the first electrode and the second electrode may be from 900 µm to 1,500 µm.

The sensor according to the first embodiment of the present disclosure may further include a circuit insulating layer disposed on at least a portion of the circuit wiring and having a window to expose the first electrode and the second electrode, wherein a thickness of the circuit insulating layer may be thicker than the first electrode and the second electrode, and may be from 800 nm to 30 µm.

The first electrode and the second electrode each may include a first end portion, a second end portion, and a central portion between the first end portion and the second end portion in a lengthwise direction, wherein the window may expose the central portion.

A length of the central portion may be from 500 µm to 2,000 µm.

The sensor according to the first embodiment of the present disclosure may further include an antenna insulating layer in which a material and a thickness thereof are identical to those of the circuit insulating layer and disposed on at least a portion of the antenna pattern, and an antenna bridge disposed on the antenna insulating layer, connecting two portions of the antenna pattern to each other, and connecting the antenna pattern and the circuit wiring to each other.

At least one of the antenna pattern, the first electrode, the second electrode, and the circuit wiring may include solid particles of at least one selected from silver (Ag), copper (Cu), and aluminum (Al) each having a spherical or flake shape, and organic matters of at least one selected from polyethylene oxide (PEO) series, oleic acid series, acrylate series, acetate series, and epoxy series.

At least one of the antenna pattern, the first electrode, the second electrode, and the circuit wiring may have pores.

The substrate may include: a soft plastic layer; and a silica layer formed between the plastic layer and the antenna pattern, the first electrode, the second electrode, and the circuit wiring.

A line width of the antenna pattern may be from 500 μm to 1,500 μm, and a spacing between lines of the antenna pattern may be from 300 μm to 700 μm.

The antenna pattern, the sensing electrode, and the circuit wiring may be formed of powder ink or paste, wherein the powder ink or the paste may be composed of solid particles of at least one selected from silver (Ag), copper (Cu), and aluminum (Al) for 40 to 70 weight percent, and organic matters of at least one selected from polyethylene oxide (PEO) series, oleic acid series, acrylate series, acetate series, and epoxy series for 30 to 60 weight percent.

The powder ink or the paste may be composed of solvent of at least one selected from a group consisting of acetone, allyl alcohol, acetic acid, acetol, methylalcohol, and benzene.

A sensor according to a second embodiment of the present disclosure may include a substrate, an antenna pattern formed in a spiral shape on the substrate and configured to receive a radio signal from an external device so as to transmit a digital signal to the external device, a first electrode and a second electrode formed on the substrate and spaced apart from each other in parallel and configured to sense a measurement value representing a change in inputted alternating current power corresponding to a change in impedance by a sensing target material being brought into contact therewith, a circuit wiring formed to be connected to each of the first electrode and the second electrode, and an element bonded to the antenna pattern and the circuit wiring, wherein the antenna pattern, the first electrode, the second electrode, and the circuit wiring may be formed of a same material and form a same layer.

Wherein the element may generate the alternating current power with the radio signal to supply the alternating current power to the first electrode and the second electrode through the circuit wiring, and generate the digital signal corresponding to the measurement value to transmit the digital signal to the external device through the antenna pattern.

A sensor according to a third embodiment of the present disclosure may include a substrate, an antenna pattern formed in a spiral shape on the substrate and configured to receive a radio signal from an external device so as to transmit a digital signal to the external device, a first electrode and a second electrode formed on the substrate and spaced apart from each other in parallel and configured to sense a measurement value representing a change in inputted alternating current power corresponding to a change in impedance by a sensing target material being brought into contact therewith, a circuit wiring formed to be connected to each of the first electrode and the second electrode, and an element bonded to the antenna pattern and the circuit wiring. Wherein the element may include a communicator receiving the radio signal from the antenna pattern and supplying the digital signal to be transmitted through the antenna pattern, a power generator generating direct current power with the radio signal, and a controller woken up by the direct current power to convert the direct current power into alternating current power so as to supply the converted direct current power to the first electrode and the second electrode, and when the sensing target material is brought into contact therewith, generating the digital signal corresponding to at least one of ion concentration representing water quality of the sensing target material or salinity of the sensing target material according to a measurement voltage corresponding to an impedance change between the first electrode and the second electrode to thereby supply the digital signal to the communicator.

When the radio signal is a signal requesting measurement of the ion concentration, the controller may control the power generator so that a first driving current set by the direct current power is supplied to the first electrode and the second electrode, and when the measurement voltage satisfies a set first ion reference voltage, the controller may generate the digital signal corresponding to the ion concentration calculated by applying the measurement voltage to a set first logarithmic function.

When the measurement voltage does not satisfy the first ion reference voltage, the controller may control the power generator so that a second driving current lower than the first driving current set by the direct current power is supplied to the first electrode and the second electrode, and when the measurement voltage satisfies a second ion reference voltage, the controller may generate the digital signal corresponding to the ion concentration calculated by applying the set measurement voltage to a second logarithmic function that is different from the first logarithmic function.

When the measurement voltage for the second driving current does not satisfy the second ion reference voltage, the controller may generate the digital signal corresponding to the ion concentration calculated by applying the measurement voltage to a set primary single equation.

When the radio signal is a signal requesting measurement of salinity, the controller may control the power generator so that driving voltage set by the direct current power is supplied to the first electrode and the second electrode, and when a sampling voltage obtained by sampling the measurement voltage according to a set sampling cycle falls within a range of a second sampling voltage value greater than a range of a set first sampling voltage value after a predetermined time has passed, the controller may generate the digital signal corresponding to salinity calculated by applying the sampling voltage to a set primary single equation.

When the sampling voltage falls within the range of the first sampling voltage value, the controller may control the power generator so that the driving voltage is re-supplied to the first electrode and the second electrode, and when the sampling voltage obtained by sampling the measurement voltage according to the sampling cycle falls within the range of the first sampling voltage value, the controller may generate the digital signal corresponding to salinity calculated by applying the sampling voltage to a set third logarithmic function.

When the sampling voltage does not fall within the range of the first sampling voltage value, the controller may determine that the sampling voltage falls within the range of the second sampling voltage value and generate the digital signal corresponding to salinity calculated by applying the sampling voltage to the primary single equation.

When the radio signal is a signal requesting measurement of the salinity and including temperature of the sensing target material, the controller may control the power generator so that driving voltage set by the direct current power is supplied to the first electrode and the second electrode, and when the temperature of the sensing target material falls within a first temperature range and a sampling voltage obtained by sampling the measurement voltage according to a set sampling cycle falls within a range of a second temperature sampling voltage value greater than a range of a first temperature sampling voltage value, the controller may generate the digital signal corresponding to salinity calculated by applying the sampling voltage to a set primary single equation.

When the sampling voltage falls within the range of the first temperature sampling voltage value, the controller may control the power generator so that the driving voltage is re-supplied to the first electrode and the second electrode, and when the sampling voltage obtained by sampling the measurement voltage according to the sampling cycle falls within the range of the first temperature sampling voltage value, the controller may generate the digital signal corresponding to salinity calculated by applying the sampling voltage to a set fourth logarithmic function.

When the sampling voltage does not fall within the range of the first temperature sampling voltage value, the controller may determine that the sampling voltage falls within the range of the second temperature sampling voltage value and generate the digital signal corresponding to salinity calculated by applying the sampling voltage to the primary single equation.

When the radio signal is a signal requesting measurement of the salinity and including temperature of the sensing target material, the controller may control the power generator so that driving voltage set by the direct current power is supplied to the first electrode and the second electrode, and when the temperature of the sensing target material falls within a range of a second temperature and a sampling voltage obtained by sampling the measurement voltage according to a set sampling cycle falls within a range of a fourth temperature sampling voltage value greater than a range of a third temperature sampling voltage value, the controller may generate the digital signal corresponding to salinity calculated by applying the sampling voltage to a set fifth logarithmic function.

When the sampling voltage falls within the range of the third temperature sampling voltage value, the controller may control the power generator so that the driving voltage is re-supplied to the first electrode and the second electrode, and when the sampling voltage obtained by sampling the measurement voltage according to the sampling cycle falls within the range of the third temperature sampling voltage value, the controller may generate the digital signal corresponding to salinity calculated by applying the sampling voltage to a set sixth logarithmic function.

When the sampling voltage does not fall within the range of the third temperature sampling voltage value, the controller may determine that the sampling voltage falls within the range of the fourth temperature sampling voltage value and generate the digital signal corresponding to salinity calculated by applying the sampling voltage to a seventh logarithmic function.

The measurement voltage may be from 0.1 V to 4 V.

A method for operating a sensor according to the present disclosure may include: generating direct current power with a radio signal by receiving the radio signal from an external device; determining whether the radio signal is a signal requesting measurement of the ion concentration representing water quality of a sensing target material or a signal requesting measurement of salinity of the sensing target material by being woken up by the direct current power; supplying a first driving current to a first electrode and a second electrode to sense a first measurement voltage corresponding to an impedance change of the first electrode and the second electrode to which the sensing target material is brought into contact with when the radio signal is determined to be the signal requesting measurement of ion concentration; determining whether the first measurement voltage satisfies a set ion reference voltage; and transmitting a first digital signal corresponding to the ion concentration calculated by applying the first measurement voltage to a set first logarithmic function to the external device when the first measurement voltage satisfies the ion reference voltage.

The method for operating the sensor according to the present disclosure may further include: when the first measurement voltage does not satisfy the ion reference voltage, supplying a second driving current lower than the first driving current to the first electrode and the second electrode; determining whether a second measurement voltage sensed at the first electrode and the second electrode by the second driving current satisfies the ion reference voltage; and when the second measurement voltage satisfies the ion reference voltage, transmitting a second digital signal corresponding to the ion concentration calculated by applying the second measurement voltage to a set second logarithmic function to the external device.

The method for operating the sensor according to the present disclosure may further include: when the second measurement voltage does not satisfy the ion reference voltage, generating a third digital signal corresponding to the ion concentration calculated by applying the second measurement voltage to a set primary single equation so as to transmit the third digital signal to the external device.

The method for operating the sensor according to the present disclosure may further include: when the radio signal is determined to be a signal requesting measurement of salinity, supplying driving voltage to the first electrode and the second electrode to sense a third measurement voltage corresponding to the impedance change of the first electrode and the second electrode to which the sensing target material is brought into contact with; determining whether a predetermined time has passed after the driving voltage is supplied; receiving the third measurement voltage sensed at the first electrode and the second electrode when the predetermined time has passed; determining whether the first sampling voltage obtained by sampling the third measurement voltage according to a set sampling cycle falls within either a range of a set first sampling voltage value or a range of a second sampling voltage value greater than the first sampling voltage value; and when the first sampling voltage falls within the range of the second sampling voltage value, generating a fourth digital signal corresponding to salinity calculated by applying the first sampling voltage to a set primary single equation so as to transmit the fourth digital signal to the external device.

The method for operating the sensor according to the present disclosure may further include: when the first sampling voltage falls within the range of the first sampling voltage value, re-supplying the driving voltage to the first electrode and the second electrode and receiving a fourth measurement voltage sensed at the first electrode and the second electrode; determining whether the second sampling voltage obtained by sampling the fourth measurement voltage according to the sampling cycle falls within the range of the first sampling voltage value; and generating a fifth digital signal corresponding to salinity calculated by applying the second sampling voltage to a set third logarithmic function so as to transmit the fifth digital signal to the external device when the second sampling voltage falls within the range of the first sampling voltage value.

The method for operating the sensor according to the present disclosure may further include, when the second sampling voltage does not fall within the range of the first sampling voltage value, determining that the second sampling voltage falls within the range of the second sampling voltage value and generating a sixth digital signal corresponding to salinity calculated by applying the second sampling voltage to the primary single equation so as to transmit the sixth digital signal to the external device.

The method for operating the sensor according to the present disclosure may further include: when the radio signal is confirmed to be a signal requesting measurement of the salinity and including temperature of the sensing target material in the determining whether the radio signal is the signal requesting measurement, determining whether the temperature of the sensing target material falls within either a first temperature range or a second temperature range; supplying driving voltage to the first electrode and the second electrode to sense a fifth measurement voltage corresponding to the impedance change of the first electrode and the second electrode to which the sensing target material is brought into contact with when the temperature of the sensing target material falls within the first temperature range; receiving the fifth measurement voltage sensed at the first electrode and the second electrode; determining whether a third sampling voltage obtained by sampling the fifth measurement voltage according to a set sampling cycle falls within either a range of a set first temperature sampling voltage value or a range of a second temperature sampling voltage value greater than the first temperature sampling voltage value; and when the third sampling voltage falls within the range of the second sampling voltage value, generating a seventh digital signal corresponding to salinity calculated by applying the third sampling voltage to a set primary single equation so as to transmit the seventh digital signal to the external device.

The method for operating the sensor according to the present disclosure may further include: when the third sampling voltage falls within the range of the first temperature sampling voltage value, re-supplying the driving voltage to the first electrode and the second electrode and receiving a sixth measurement voltage sensed at the first electrode and the second electrode; determining whether a fourth sampling voltage obtained by sampling the sixth measurement voltage according to the sampling cycle falls within the range of the first temperature sampling voltage value; and when the fourth sampling voltage falls within the range of the first temperature sampling voltage value, generating an eighth digital signal corresponding to salinity calculated by applying the fourth sampling voltage to a set fourth logarithmic function so as to transmit the eighth digital signal to an external device.

The method for operating the sensor according to the present disclosure may further include, when the fourth sampling voltage does not fall within the range of the first temperature sampling voltage value, determining that the fourth sampling voltage falls within the range of the second temperature sampling voltage value and generating a ninth digital signal corresponding to salinity calculated by applying the fourth sampling voltage to a set primary single equation so as to transmit the ninth digital signal to the external device.

The method for operating the sensor according to the present disclosure may further include: when the temperature of the sensing target material falls within the second temperature range, supplying the driving voltage to the first electrode and the second electrode to sense a seventh measurement voltage corresponding to the impedance change of the first electrode and the second electrode to which the sensing target material is brought into contact with; receiving the seventh measurement voltage sensed at the first electrode and the second electrode; determining whether a fifth sampling voltage obtained by sampling the seventh measurement voltage according to a sampling cycle falls within either a range of a set third temperature sampling voltage value or a range of a fourth temperature sampling voltage value greater than the third temperature sampling voltage value; and when the fifth sampling voltage falls within the range of the fourth temperature sampling voltage value, generating a ninth digital signal corresponding to salinity calculated by applying the fifth sampling voltage to a set fifth logarithmic function so as to transmit the ninth digital signal to the external device.

The method for operating the sensor according to the present disclosure may further include: when the fifth sampling voltage falls within the range of the third temperature sampling voltage value, re-supplying the driving voltage to the first electrode and the second electrode and receiving a seventh measurement voltage sensed at the first electrode and the second electrode; determining whether a sixth sampling voltage obtained by sampling the seventh measurement voltage according to the sampling cycle falls within the range of the third temperature sampling voltage value; and when the sixth sampling voltage falls within the range of the third temperature sampling voltage value, generating a tenth digital signal corresponding to salinity calculated by applying the sixth sampling voltage to a set sixth logarithmic function so as to transmit the tenth digital signal to the external device.

The method for operating the sensor according to the present disclosure may further include, when the sixth sampling voltage does not fall within the range of the third temperature sampling voltage value, determining that the sixth sampling voltage falls within the range of the fourth temperature sampling voltage value to generate an eleventh digital signal corresponding to salinity calculated by applying the sixth sampling voltage to a set seventh logarithmic function.

Advantageous Effects

A sensor and a method for operating the sensor according to the present disclosure have an advantage of simplifying a manufacturing process by forming an antenna pattern, a sensing electrode, and a circuit wiring of a same material and forming the antenna pattern, the sensing electrode, and the circuit wiring on a same layer.

In addition, a sensor and a method for operating the sensor according to the present disclosure have an advantage of suppressing oxidation and corrosion of a sensing electrode by forming the sensing electrode to have a curvature when measuring salinity and water quality of a sensing target material.

In addition, a sensor and a method for operating the sensor according to the present disclosure have an advantage of decreasing a volume of a separate power source and lowering manufacturing cost by measuring salinity and water quality of a sensing target material with direct current power generated by harvesting energy from a radio signal received from an external device.

In addition, in a sensor and a method for operating the sensor according to the present disclosure, the sensor is capable of generating direct current power by harvesting energy from a radio signal received from an external device to transmit a digital signal corresponding to a result of measuring salinity and water quality of a sensing target material to the external device, and has an enhanced portability.

In addition, various effects other than the above-described effects may be directly or implicitly disclosed in a detailed description according to embodiments of the present disclosure to be described later.

MODES FOR CARRYING OUT PREFERRED EMBODIMENTS

Figure 1:
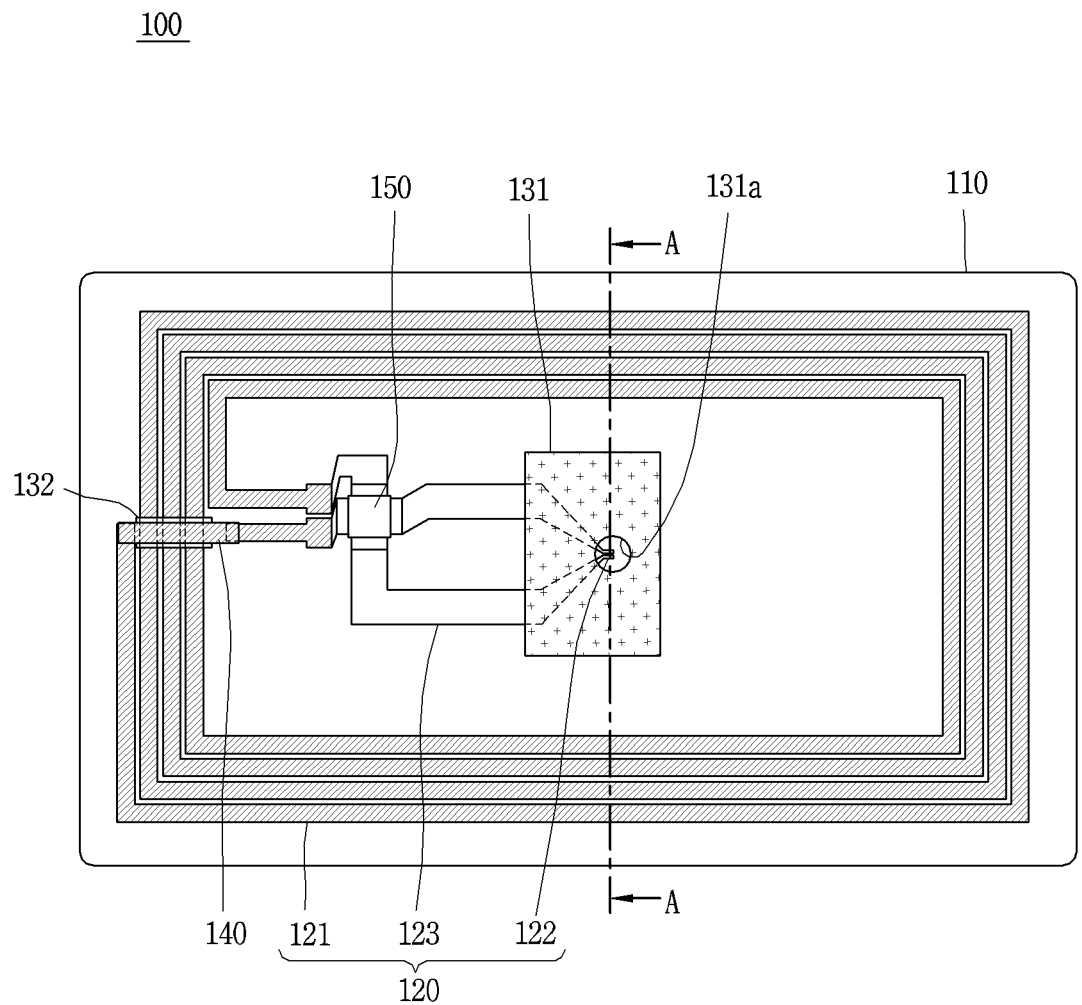
FIG. 1 is a planar view of a sensor according to the present disclosure.

In the following description, it should be noted that only parts needed in understanding the embodiments of the present disclosure will be described, and descriptions of other parts will be omitted so as not to divert the gist of the present disclosure.

Terms or words used in this specification and claims described below should not be construed as being limited to a conventional or dictionary meaning, and it should be interpreted as a meaning and concept consistent with the technical idea of the present disclosure on the basis of the principle that an inventor can properly define the concept of terms in order to explain his or her disclosure in the best way. Therefore, the embodiments described in this specification and the configurations illustrated in the drawings are only preferred embodiments of the present disclosure, and do not represent all the technical ideas of the present disclosure, and it should be understood that there may be various equivalents and variations that can replace them at the time of application.

Hereinafter, embodiments of the present disclosure will be described in more detail with reference to the accompanying drawings.

FIG. 1 is a planar view of a sensor according to the present disclosure.

Referring to FIG. 1, a sensor 100 may include a substrate 110, a conductive layer 120, a circuit insulating layer 131, an antenna insulating layer 132, an antenna bridge 140, and an element 150.

The substrate 110 may have a shape of a flat plate as a whole.

The substrate 110 may be configured to support the conductive layer 120, the circuit insulating layer 131, the antenna insulating layer 132, the antenna bridge 140, and the element 150.

The conductive layer 120, the circuit insulating layer 131, the antenna insulating layer 132, the antenna bridge 140, and the element 150 may be formed or mounted on the substrate 110 by various processes.

The substrate 110 may have flexibility.

In an embodiment, since the sensor 100 has a very thin thickness, the sensor 100 may be easily damaged by an external force when the sensor 100 does not have flexibility. However, when the substrate 110 has flexibility, the sensor 100 may have high reliability even in repetitive mechanical deformation.

The substrate 110 may be formed of soft plastic (polymer compound or synthetic resin).

The plastic may contain at least one selected from a group consisting of, for example, polyethylene terephthalate (PET), polyimide (PI), polystyrene (PS), and polyethylene naphthalate (PEN).

The substrate 110 may further include a silica layer 112. The silica layer 112 will be described later with reference to FIG. 2.

The conductive layer 120 may be formed as a single layer on one surface of the substrate 110.

The conductive layer 120 may be formed by a printing process. The conductive layer 120 may include an antenna pattern 121, a circuit wiring 123, and a sensing electrode 122.

The antenna pattern 121, the sensing electrode 122, and the circuit wiring 123 may be integrally formed. The expression "integrally formed" means that the antenna pattern 121, the sensing electrode 122, and the circuit wiring 123 are not physically separated from each other.

However, the antenna pattern 121, the sensing electrode 122, and the circuit wiring 123 are not necessarily integrally formed. The antenna pattern 121, the sensing electrode 122, and the circuit wiring 123 are classified solely by functions of the conductive layer 120.

The conductive layer 120 including the antenna pattern 121, the sensing electrode 122, and the circuit wiring 123 may be simultaneously formed by a single printing process, and may form a same layer on the substrate 110.

The expression "forming a same layer" means that the antenna pattern 121, the sensing electrode 122, and the circuit wiring 123 form one layer on the substrate 110, and thicknesses or heights of the antenna pattern 121, the sensing electrode 122, and the circuit wiring 123 may or may not be same as each other.

The conductive layer 120 including the antenna pattern 121, the sensing electrode 122, and the circuit wiring 123 may be formed of a same material that may be simultaneously formed by a single printing process.

Various methods such as screen printing, gravure printing, and inkjet printing may be used for the printing process.

The antenna pattern 121 may be configured to transmit and receive a radio signal to and from an external device.

An external device refers to an electronic device having a wired or wireless communication function.

Examples of such device include cellular phones, smart phones, desktop computers, laptop computers, digital broadcast terminals, personal digital assistants (PDAs), portable multimedia players (PMPs), navigators, slate PCs, tablet PCs, ultra books, and the like.

The antenna pattern 121 transmits or receives a radio signal to or from an external device.

In an embodiment, the sensor 100 does not include a power supply, such as a battery. The sensor 100 generates direct current power by using a radio signal received from an external device through the antenna pattern 121 and uses the direct current power to operate the sensor 100. In addition, the sensor 100 is configured to transmit a sensing result to the external device through the antenna pattern 121.

The antenna pattern 121 extends in a two-dimensional spiral shape.

The two-dimensional spiral shape means that the antenna pattern 121 is wound from edges of the substrate 110 to a central region of the substrate 110 as illustrated in FIG. 1. This may also be described such that the antenna pattern 121 is wound from the central region of the substrate 110 to the edges of the substrate 110. However, in the present disclosure, the two-dimensional spiral shape does not necessarily refer to a curve, and has a concept including a straight line as in FIG. 1.

The antenna pattern 121 has a line width of 500 µm to 1,500 µm to have high inductance. A spacing between lines forming a two-dimensional spiral is preferably set to 300 µm to 700 µm in order to have an appropriate capacitance component.

The antenna pattern 121 may operate as a radiator of a near field communication (NFC) antenna. The near field communication antenna refers to a communication device in which information is exchanged using a communication standard of 13.56 MHz.

The sensing electrode 122 is configured to cause an impedance change by being brought into contact with a sensing target material.

When a radio signal is received from an external device through the antenna pattern 121, the sensor 100 generates direct current power by using the radio signal. When direct current power is generated, a remaining portion of the sensor 100 is operated, and an alternating current power is inputted to the sensing electrode 122. Therefore, the sensing electrode 122 is operated only when the radio signal is received through the antenna pattern 121.

When the sensing electrode 122 that has received alternating voltage is brought into contact with the sensing target material, an impedance change occurs. Since the impedance change causes a change in alternating current power, the sensor 100 may detect salinity, sugar content of the sensing target material, rancidity of fat and oil, and the like from the impedance change or the change in alternating current power.

As the sensing target material, any material causing an impedance change on the sensing electrode 122 may be applied. Foods with salt and sugar, agricultural products with residual pesticides, and fat and oil in which a rancidity thereof can be checked are examples of the sensing target material. Not only liquid but also gas may be the sensing target material.

The circuit wiring 123 electrically connects the antenna pattern 121 and the sensing electrode 122. In addition, the circuit wiring 123 is electrically connected to the element 150 that controls the sensor 100. The circuit wiring 123 may be understood as indicating a remaining region of the conductive layer 120 excluding the antenna pattern 121 and the sensing electrode 122.

The insulating layers 131 and 132 are disposed on the conductive layer 120 to cover the conductive layer 120.

The insulating layers 131 and 132 include the circuit insulating layer 131 and the antenna insulating layer 132. The circuit insulating layer 131 and the antenna insulating layer 132 may be simultaneously formed by a single printing process, and may form a same layer on the conductive layer 120.

The expression "forming a same layer" means that the circuit insulating layer 131 and the antenna insulating layer 132 are formed to have a height same as each other on the conductive layer 120.

Unlike the above description, the expression "forming a same layer" may also be interpreted that the circuit insulating layer 131 and the antenna insulating layer 132 are simultaneously formed on the conductive layer 120 by a single printing process. The circuit insulating layer 131 and the antenna insulating layer 132 can be simultaneously formed by a single printing process because they are formed of a same material.

The circuit insulating layer 131 is disposed to cover at least a portion of the circuit wiring 123. The circuit insulating layer 131 may also be disposed to partially cover the sensing electrode 122. The circuit insulating layer 131 has a flat plate shape.

The circuit insulating layer 131 is provided with a window 131a (or a hole) to expose the sensing electrode 122. Since the circuit insulating layer 131 is provided with the window 131a, the sensing electrode 122 can be exposed through the window 131a even if the circuit insulating layer 131 is disposed to cover the entire sensing electrode 122.

The window 131a may set an exposed length of the sensing electrode 122, which will be described later with reference to FIG. 4.

The circuit insulating layer 131 serves to prevent liquid to be brought into contact with the sensing electrode 122 from flowing into the circuit wiring 123 to cause a malfunction of the sensor 100. Since the circuit insulating layer 131 has a predetermined height (in a thickness direction of the sensor 100), the circuit insulating layer 131 acts as a barrier preventing an inflow of liquid. Accordingly, the sensing target material may form a droplet within an area defined by the window 131a.

The circuit insulating layer 131 has a surface energy (or surface tension) greater than that of the substrate 110. When the circuit insulating layer 131 has a surface energy smaller than that of the substrate 110, liquid in contact with the sensing electrode 122 may not form a droplet but spread widely, and therefore, the sensing electrode 122 may not sufficiently sense the target material. On the other hand, when the circuit insulating layer 131 has a surface energy greater than that of the substrate 110 as in the present disclosure, the liquid forms a droplet and the sensing electrode 122 may sufficiently sense the target material.

Since the antenna pattern 121 has the two-dimensional spiral shape, the antenna pattern 121 itself serves as a boundary to have an outer side and an inner side. The antenna bridge 140 is configured to connect the outer side and the inner side of the antenna pattern 121 to each other, but the antenna bridge 140 cannot be directly disposed on the antenna pattern 121. The antenna insulating layer 132 serves to insulate the antenna pattern 121 and the antenna bridge 140.

The antenna insulating layer 132 is disposed to cover a portion of the antenna pattern 121. Referring to FIG. 1, it can be seen that the antenna insulating layer 132 is covering a left portion of the antenna pattern 121. In addition, the antenna insulating layer 132 extends in a direction crossing any of the above. As the antenna insulating layer 132 is disposed between the antenna pattern 121 and the antenna bridge 140, insulation may be formed between the antenna pattern 121 and the antenna bridge 140.

The antenna insulating layer 132 may be formed in multiple layers, and each layer may be formed by different printing processes. When the antenna insulating layer 132 is formed in multiple layers, a lower layer may be referred to as a first antenna insulating layer 132a (see FIG. 2), and an upper layer may be referred to as a second antenna insulating layer 132b (see FIG. 2). When the circuit insulating layer 131 and the first antenna insulating layer 132a are formed in a single printing process and then the second antenna insulating layer 132b is additionally printed in a following printing process, the circuit insulating layer 131 has one layer and the antenna insulating layer 132 has two layers.

The antenna bridge 140 is disposed on the antenna insulating layer 132 to cover the antenna insulating layer 132. One end of the antenna bridge 140 is connected to one end of the antenna pattern 121 disposed at the outer side of the antenna pattern 121 and extends across the antenna pattern 121. Another end of the antenna bridge 140 is connected to one end of the circuit wiring 123 disposed at the inner side of the antenna pattern 121. Alternatively, the antenna bridge 140 may connect the inner side and the outer side of the antenna pattern 121.

The element 150 is mounted on the substrate 110 and is electrically connected to the circuit wiring 123.

Various electrical and electronic configurations related to the operation of the sensor 100 may be implemented by the element 150.

A radio signal received through the antenna pattern 121 is transmitted to the element 150 through the circuit wiring 123. In addition, alternating voltage is also inputted to the sensing electrode 122 through the circuit wiring 123.

Hereinafter, a multilayer structure of the sensor 100 will be described with reference to FIG. 2.

Figure 2:
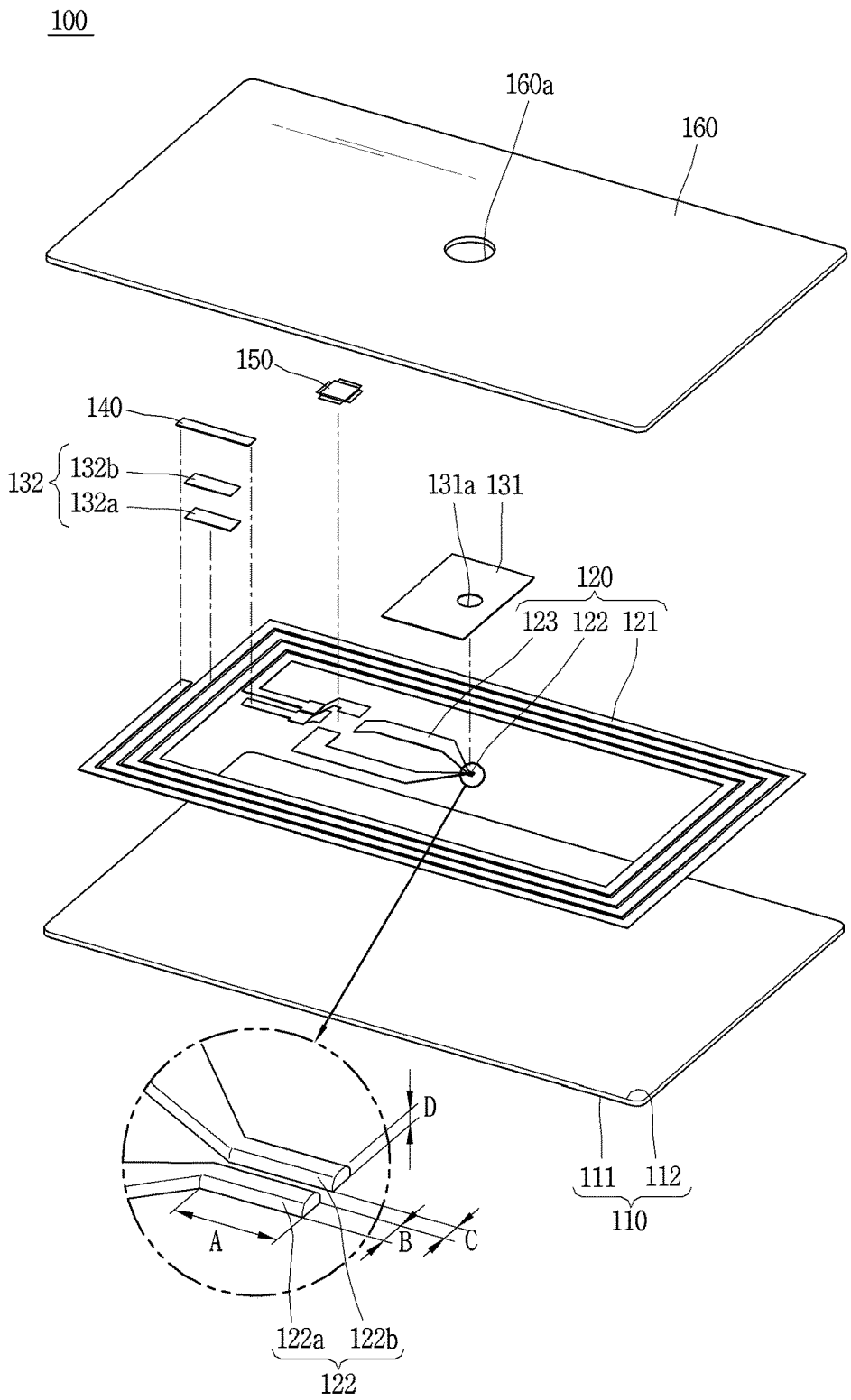
FIG. 2 is an exploded perspective view of a sensor according to the present disclosure.

FIG. 2 is an exploded perspective view of the sensor according to the present disclosure.

In FIG. 2, it is visually checked that the antenna pattern 121, the sensing electrode 122, and the circuit wiring 123 form a same layer, and the circuit insulating layer 131 and the antenna insulating layer 132 also form a same layer.

The substrate 110 includes a plastic layer 111 and the silica layer 112.

The plastic layer 111 is formed of a soft plastic (polymer compound or synthetic resin). The plastic may contain at least one selected from a group consisting of polyethylene terephthalate (PET), polyimide (PI), polystyrene (PS), and polyethylene naphthalate (PEN).

The silica layer 112 is coated on one surface of the plastic layer 111. The silica layer 112 is formed between the plastic layer 111 and the conductive layer 120. The silica layer 112 is for rapid spread of a sensing target solution, stabilization of the sensing target solution, and strengthening of adhesion strength of the conductive layer 120. The silica layer 112 may have a thickness of several nm to several tens of nm.

The conductive layer 120 is formed as a single layer. In addition, the antenna pattern 121, the sensing electrode 122, and the circuit wiring 123 may be integrally formed, and form a same layer (or a single layer). The expression "integrally formed" means that the antenna pattern 121, the sensing electrode 122, and the circuit wiring 123 are not physically separated from each other. However, the antenna pattern 121, the sensing electrode 122, and the circuit wiring 123 are not necessarily integrally formed.

The meaning of the conductive layer 120 being formed as a single layer is substantially the same as the meaning of the antenna pattern 121, the sensing electrode 122, and the circuit wiring 123 forming a same layer. The conductive layer 120 can be formed as a single layer, or the antenna pattern 121, the sensing electrode 122, and the circuit wiring 123 can form a same layer, because the antenna pattern 121, the sensing electrode 122, and the circuit wiring 123 are formed of a same material.

The conductive layer 120 is formed by a printing process. When the antenna pattern 121, the sensing electrode 122, and the circuit wiring 123 are respectively formed by different printing processes, the antenna pattern 121, the sensing electrode 122, and the circuit wiring 123 each forms different layers. As a result, the conductive layer 120 will be formed in multiple layers rather than a single layer.

However, when the antenna pattern 121, the sensing electrode 122, and the circuit wiring 123 are formed of a same material as in the present disclosure, a single-layered conductive layer 120 can be formed by a single printing process. In addition, the conductive layer 120 formed in this way is divided into three portions according to functions, wherein a first portion is the antenna pattern 121, a second portion is the sensing electrode 122, and a third portion is the circuit wiring 123.

When the antenna pattern 121, the sensing electrode 122, and the circuit wiring 123 form a same layer (or a single layer), the sensor 100 has several advantages over the related art.

First, since a thickness of the sensor 100 can be reduced, the sensor 100 can be more compact than the related art. When the sensor 100 is miniaturized, portability of the sensor 100 can be enhanced.

In addition, since a manufacturing process of the sensor 100 becomes simpler, the sensor 100 can be manufactured at a lower cost than the related art. High price makes it difficult for the sensor 100 to be popularized, but when the sensor 100 can be manufactured at an inexpensive unit price according to the present disclosure, it may contribute to the popularization of the sensor 100.

Finally, a process error does not occur among the antenna pattern 121, the sensing electrode 122, and the circuit wiring 123. When the antenna pattern 121, the sensing electrode 122, and the circuit wiring 123 are sequentially formed by different printing processes, the sensor 100 may not be manufactured according to the original design due to a process error (especially an alignment error). A process error is particularly problematic in mass production. However, the problem can be solved by forming the antenna pattern 121, the sensing electrode 122, and the circuit wiring 123 in a single printing process.

The sensing electrode 122 includes a first electrode 122a and a second electrode 122b. The first electrode 122a and the second electrode 122b extend in parallel from the circuit wiring 123, respectively, and a spacing exists between the first electrode 122a and the second electrode 122b.

Hereinafter, a structure or standard of the sensing electrode 122, more specifically, a length, width, spacing, and height of the sensing electrode 122 will be described. Referring to an enlarged portion of the sensing electrode 122 in FIG. 2, a total length, width, spacing, and height of the sensing electrode 122 are indicated as A, B, C, and D, respectively.

The total length A of the sensing electrode 122 may be 400 μm to 5,000 μm, and an exposed length of the sensing electrode 122 exposed through the window 131a (A', a length corresponding to E in FIG. 4) may be 50 μm to 5,000 μm. For reference, the sensing electrode 122 illustrated in FIG. 1 is entirely exposed rather than being partially exposed through the window 131a. Therefore, the exposed length A' of the sensing electrode 122 exposed through the window 131a is same as the total length A of the sensing electrode 122. However, as will be described later in FIG. 4, the exposed length of the sensing electrode 122 exposed through the window 131a and the total length of the sensing electrode 122 are not always the same.

The exposed length A' of the sensing electrode 122 exposed through the window 131a affects a resolution of the sensor 100, print reproducibility according to mass production, and reliability of the sensor 100. As the exposed length of the sensing electrode 122 exposed through the window 131a decreases, the resolution of the sensor 100 may be improved.

For example, when the exposed length A' of the sensing electrode 122 exposed through the window 131a is about 300 to 500 μm, the resolution of the sensor 100 can be greatly improved. However, it is difficult to accurately position and print the window 131a on the sensing electrode 122 during a production process of the sensor 100. Therefore, the exposed length A' of the sensing electrode 122 is preferably longer than 300 μm. In addition, when the total length A of the sensing electrode 122 is shorter than 400 μm, the exposed length A' of the sensing electrode 122 exposed through the window may be inconsistent due to an occurrence of a positional error of the window 131a caused by mass production. In addition, when the total length A of the sensing electrode 122 is shorter than 400 μm, an impedance increases as a number of times of use of the sensor 100 increases, thereby deteriorating durability and reliability of the sensing electrode 122.

Therefore, it is preferable that the total length A of the sensing electrode 122 is longer than 400 μm. In addition, in order to secure the resolution of the sensor 100, the exposed length of the sensing electrode 122 is preferably shorter than 2,000 μm. In addition, the total length A of the sensing electrode 122 can also be up to 5,000 μm.

The width B of the sensing electrode 122 may be 50 μm to 1,000 μm. As the width B of the sensing electrode 122 decreases, the resolution of the sensor 100 can be improved. However, when the width B of the sensing electrode 122 is too narrow, a printing process of the conductive layer 120 may be unstable. Therefore, for a stable printing process, the width B of the sensing electrode 122 is preferably 50 μm to 200 μm.

The spacing C between the first electrode 122a and the second electrode 122b may be 50 μm to 3,000 μm. However, when the spacing C is too large, this may cause insufficient operation of the sensor 100 when an amount of sensing target liquid is insufficient. The sensing target liquid has to form a droplet to be brought into contact with the first electrode 122a and the second electrode 122b both. However, when the spacing between the first electrode 122a and the second electrode 122b is too large, the liquid may be brought into contact with only one electrode. In consideration of this point, the spacing C between the first electrode 122a and the second electrode 122b is preferably 900 μm to 1,500 μm.

The height D (in a thickness direction of the sensor 100) of the sensing electrode 122 may be 700 nm to 15 μm. The height D of the sensing electrode 122 affects the thickness of the sensor 100 and durability and reliability of the sensing electrode 122. When the height D of the sensing electrode 122 is shorter than 700 nm, the sensing electrode 122 may disappear due to repeated sensing process. In addition, in consideration of limitation of the printing process and increase in the thickness of the sensor 100, the height D of the sensing electrode 122 is preferably shorter than 15 μm. Since the sensing electrode 122 is a portion of the conductive layer 120, the height D of the sensing electrode 122 refers to a height of the conductive layer 120.

A relation between the structure of the sensing electrode 122 and the resolution of the sensor 100 will be described again with reference to the graphs of FIGS. 5 and 6.

The sensor 100 includes a protective layer 160. The protective layer 160 is formed of an electrically insulating material. The protective layer is disposed to face one surface of the substrate 110 and is formed to cover all of the components of the sensor 100. The protective layer 160 is provided with a hole 160a, and the sensing electrode 122 may be exposed through the hole 160a. For better understanding for users, a mark indicating an inlet position of the sensing target liquid may be printed on an outer surface of the protective layer 160.

The circuit insulating layer 131 and the first antenna insulating layer 132a are formed by a single printing process which is similar to the antenna pattern 121, the sensing electrode 122, and the circuit wiring 123 being formed by a single printing process. Accordingly, an advantage of the circuit insulating layer 131 and the first antenna insulating layer 132a being formed by a single printing process is same as that of the antenna pattern 121, the sensing electrode 122, and the circuit wiring 123 being formed by a single printing process.

Referring to FIG. 2, it can be seen that the second antenna insulating layer 132b is disposed on the first antenna insulating layer 132a.

Figure 3:
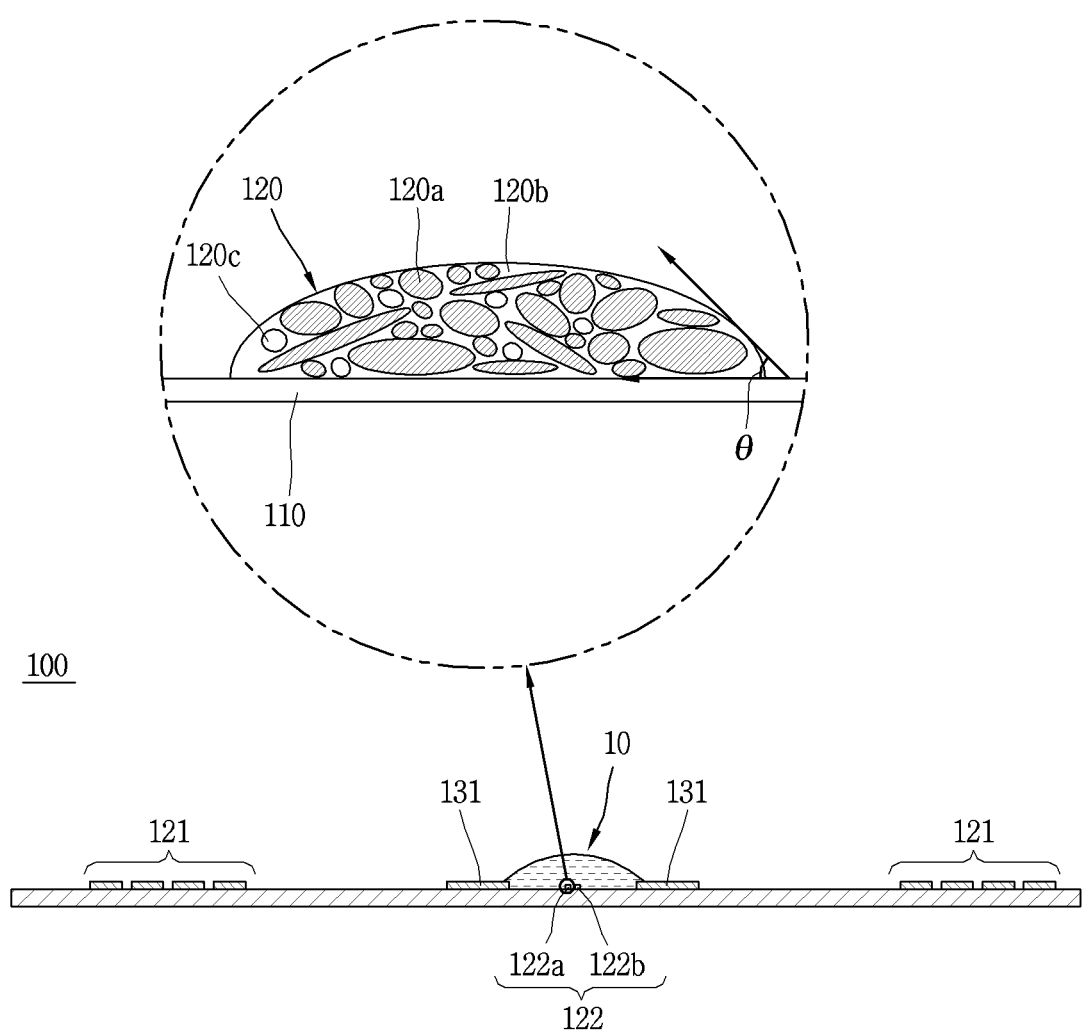
FIG. 3 is a sectional view taken along line A-A of FIG. 1.

FIG. 3 is a sectional view taken along line A-A of FIG. 1.

The circuit insulating layer 131 may have a height of 800 nm to 30 μm. The circuit insulating layer 131 has a height higher than that of the sensing electrode 122. In other words, the circuit insulating layer 131 is printed thicker than the height of the sensing electrode 122. The circuit insulating layer 131 serves as a barrier to suppress a flow of a droplet. Therefore, when the height of the circuit insulating layer 131 is shorter than the height of the sensing electrode 122, liquid in contact with the sensing electrode 122 may pass over the circuit insulating layer 131. Therefore, it is preferable that the circuit insulating layer 131 has a height higher than that of the sensing electrode 122.

Since the circuit insulating layer 131 and the antenna insulating layer 132 described in FIGS. 1 and 2 are formed of a same material, form a same layer, and are formed by a single printing process, it can be expected that the antenna insulating layer 132 also has a height of 800 nm to 30 μm. However, the antenna insulating layer 132 can be formed in multiple layers, and in this case, a height of a first layer is expected to be 800 nm to 30 μm.

FIG. 3 shows a state in which a sensing target material is in contact with the sensing electrode 122. In the drawing, it can be seen that the sensing target material in a liquid state is forming a droplet and is trapped in the window 131a by the circuit insulating layer 131.

The following description refers to an enlarged portion of the conductive layer 120 in FIG. 3.

The conductive layer 120 may be formed of solid particles 120a and organic matters 120b.

The solid particle 120a may be at least one selected from silver (Ag), copper (Cu), and aluminum (Al).

There was a technique in the related art in which a noble metal such as platinum (Pt) or gold (Au) is used as a material of the sensing electrode 122 to deposit the noble metal on the substrate 110 or sinter the noble metal at a high temperature. In the related art, the circuit wiring 123 and the sensing electrode 122 are formed on different layers. However, a noble metal increases a cost of the sensor 100. In addition, the fact that the circuit wiring 123 and the sensing electrode 122 are formed on different layers means that the circuit wiring 123 and the sensing electrode 122 do not have the advantage of the present disclosure described with reference to FIG. 2.

On the other hand, since silver (Ag), copper (Cu), and aluminum (Al) are inexpensive compared to noble metals, the sensor 100 of the present disclosure has an advantage of lowering the cost of the sensor 100 compared to the related art technology. However, silver (Ag), copper (Cu), and aluminum (Al) have a lower standard reduction potential than noble metals such as platinum (Pt) or gold (Au). Therefore, there is a concern that the sensing electrode 122 may be denatured by oxidation or corrosion during the sensing process.

In the present disclosure, a measurement voltage of the sensor 100 is limited to 0.1 V to 4 V to suppress oxidation or corrosion of the conductive layer 120. In addition, the present disclosure solves the problem of oxidation or corrosion of the conductive layer 120 by optimizing the structure of the sensing electrode 122 and the material of the conductive layer 120. The structure of the sensing electrode 122 has been described with reference to FIG. 2. Material optimization of the conductive layer 120 relates to a content of the solid particle 120a and the organic matter 120b, which will be described later with reference to FIG. 9.

In addition, the solid particle 120a has a spherical or flake shape. In the conductive layer 120 illustrated in FIG. 3, all shapes other than a spherical shape may be referred to as a flake shape. A flake-shaped solid particle 120a may have a relatively high conductivity compared to a spherical shape.

The solid particle 120a may have a size of several tens of nm to 20 μm in order to secure a reaction specific surface area. The sensing electrode 122 reacts to a sensing target material and causes an impedance change. In the impedance, a capacitance component and a resistance component exist. When the reaction specific surface area of the solid particle 120a is large, the capacitance component also increases. When the reaction specific surface area of the solid particle 120a is large, oxidation or corrosion of the sensing electrode 122 due to the reaction can be suppressed to thereby extend a lifespan of the sensor 100.

The organic matter 120b supports the solid particle 120a. The solid particle 120a exposed outwardly of the organic matter 120b may disappear after the sensing process, but the solid particle 120a existing in the organic matter 120b may be protected by the organic matter 120b. Therefore, the organic matter 120b serves to improve the durability and reliability of the sensor 100.

The organic matter 120b includes resin of at least one selected from a group consisting of polyethylene oxide (PEO) series, oleic acid series, acrylate series, acetate series, and epoxy series.

The conductive layer 120 has pores 120c. The pore 120c may have a size of several nm to several tens of μm. When the conductive layer 120 has the pores 120c, the conductive layer 120 is not easily damaged by repeated mechanical deformation, thereby improving the reliability of the sensor 100. As described in FIG. 1, since the substrate 110 has flexibility, the conductive layer 120 also preferably has the pores 120c.

The conductive layer 120 and the substrate 110 form an acute contact angle θ. The contact angle θ referred in the present disclosure is shown in FIG. 3. A cross section of the sensing electrode 122 manufactured by the related art vacuum deposition method has a rectangular shape, and forms an obtuse contact angle θ with the substrate 110. The sensing electrode 122 forming the obtuse contact angle θ may be easily separated from the substrate 110 by friction or bending. However, as in the present disclosure, the sensing electrode 122 forming the acute contact angle θ with the substrate 110 has excellent resistance to friction or bending, and can maintain durability without a separate protective layer.

Figure 4:
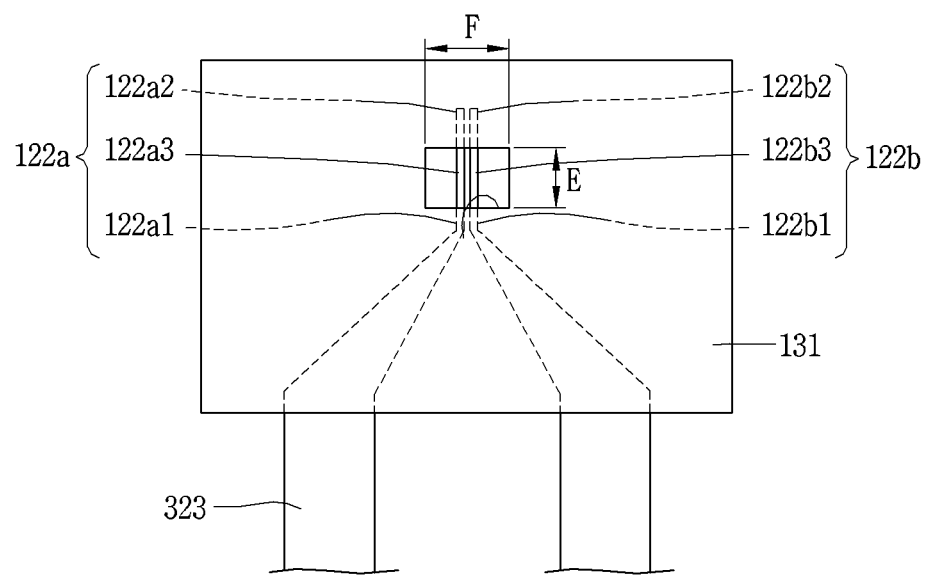
FIG. 4 is a planar view of a structure of a sensor according to the present disclosure.

FIG. 4 is a planar view of a structure of a sensor according to the present disclosure.

FIG. 4 is a conceptual diagram showing a structure of the circuit wiring 123, the sensing electrode 122, and the circuit insulating layer 131 which are advantageous for mass production.

There are process errors in mass production. Therefore, a final product may not always be manufactured as designed. In particular, the smaller the product, the greater the probability of process errors. Considering the process error, a ratio of products manufactured as designed to total manufactured products is expressed as a yield.

In an embodiment, the sensor is formed by multiple printing processes, heat drying process, and curing process. Although a possibility of process errors is very low in a single printing process, a process error (especially an alignment error) may occur when a printing process to form each layer is repeated, and even in the heat drying process, a process error may occur due to a shrinkage of a substrate (for example, the substrate 110 in FIG. 1). In particular, the substrate 110 contracts much in a lengthwise direction.

In particular, the resolution of the sensor may be determined according to the exposed length of the first electrode 122a and the second electrode 122b. However, the total length and the exposed length of the first electrode 122a and the second electrode 122b are very small, within 5,000 μm. Therefore, there is a high probability of occurrence of a process error with respect to an exposed length of the sensor during mass production of the sensor. Therefore, the resolution of the sensor can be secured only when the sensor has a structure capable of minimizing process errors.

The first electrode 122a, the second electrode 122b, the circuit wiring 123, and the circuit insulating layer 131 are all formed by the printing process, and the circuit insulating layer 131 is disposed to cover the first electrode 122a, the second electrode 122b, and the circuit wiring 123. With this reason, the circuit insulating layer 131 is formed after the first electrode 122a, the second electrode 122b, and the circuit wiring 123 are printed. Therefore, a process error may occur during a repetition of the printing process and the heat drying process. The first electrode 122a and the second electrode 122b may be exposed differently from the original design, or may not even be exposed.

FIG. 4 shows a structure of the sensor 100 to solve this problem.

The first electrode 122a and the second electrode 122b each may be divided into three portions in the lengthwise direction. The first electrode 122a has a first end portion 122a1 and a second end portion 122a2, and the second electrode 122b has a first end portion 122b1 and a second end portion 122b2 in the lengthwise direction. In addition, an area between the first end portion 122a1 and the second end portion 122a2 may be referred to as a central portion 122a3, and an area between the first end portion 122b1 and the second end portion 122b2 may be referred to as a central portion 122b3.

The circuit insulating layer 131 covers the first end portions 122a1 and 122b1 and the second end portions 122a2 and 122b2, and the window 131a exposes the central portions 122a3 and 122b3.

The first electrode 122a and the second electrode 122b are formed to be longer than a length E of the window 131a. The window 131a controls an exposed length of the central portions 122a3 and 122b3.

For example, when the length of the window 131a is 500 µm to 2,000 µm, the exposed length of the sensing electrode 122 exposed through the window 131a is always determined to be 500 µm to 2,000 µm as the window 131a exposes the central portions 122a3 and 122b3. Even if positions of the sensing electrode 122 and the circuit insulating layer 131 are slightly changed, the exposed length of the sensing electrode 122 exposed through the window 131a may be maintained at 500 µm to 2,000 µm. With this structure, the sensor of the present disclosure can obtain a high yield despite process errors of mass production.

A width F of the window 131a is wider than the spacing between the first electrode 122a and the second electrode 122b, but preferably not exceeding 5,000 µm. This is because liquid to be brought into contact with the first electrode 122a and the second electrode 122b may not form a droplet and may spread widely when the width of the window 131a is too large.

Figure 5:
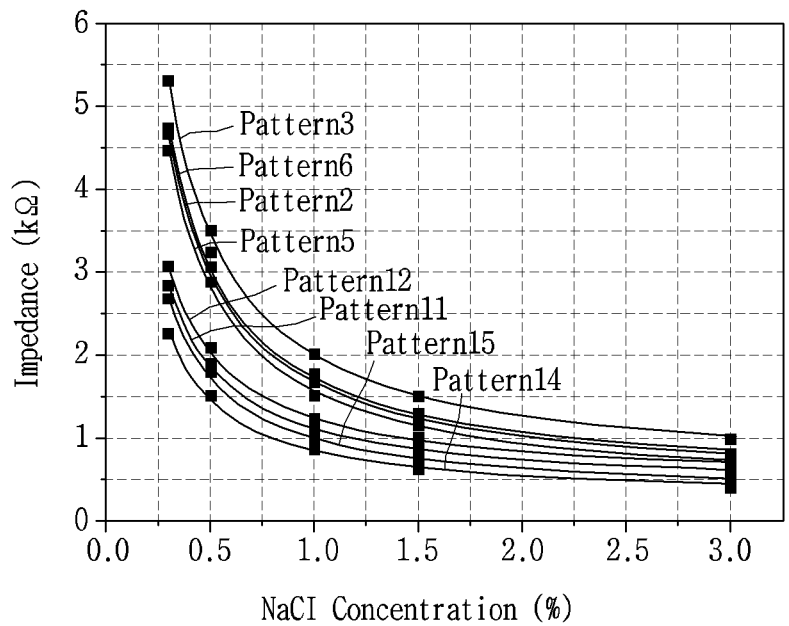
FIGS. 5 and 6 are experiment graphs showing a relation between an electrode structure and a resolution of a sensor according to the present disclosure.
Figure 6:
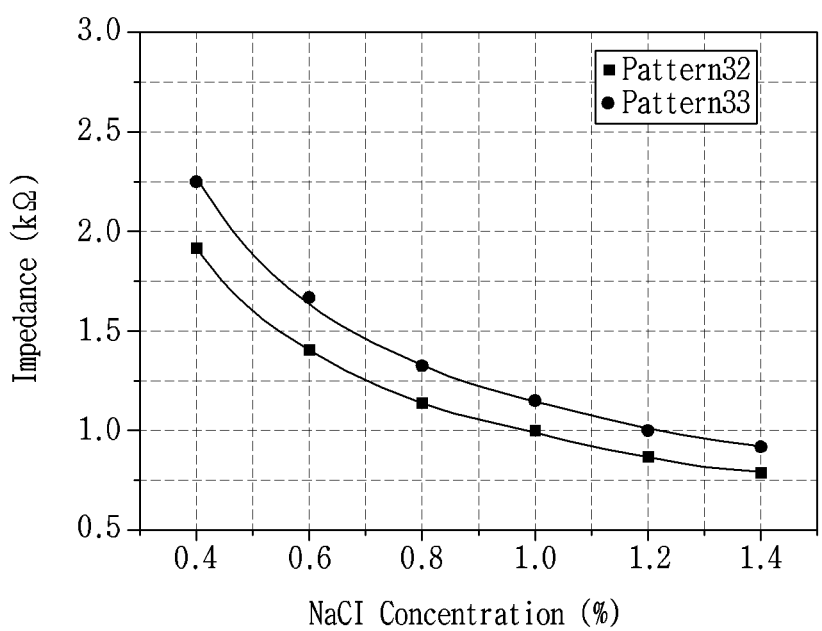

FIGS. 5 and 6 are experiment graphs showing a relation between an electrode structure and a resolution of a sensor according to the present disclosure.

In FIGS. 5 and 6, a horizontal axis of the graph denotes concentration of sodium chloride, and a vertical axis denotes impedance. Each pattern has a different sensing electrode structure. The structure of the sensing electrode refers to a length and width of the sensing electrode, and a spacing between two electrodes. The structure of the sensing electrode of each pattern is summarized in Table 1.

TABLE 1

| Pattern | Length (µm) | Width (µm) | Spacing (µm) |
|---|---|---|---|
| 2 | 500 | 100 | 200 |
| 3 | 500 | 100 | 300 |
| 5 | 500 | 200 | 200 |
| 6 | 500 | 200 | 300 |
| 11 | 1,000 | 100 | 200 |
| 12 | 1,000 | 100 | 300 |
| 14 | 1,000 | 200 | 200 |
| 15 | 1,000 | 200 | 300 |
| 32 | 1,250 | 100 | 900 |
| 33 | 1,600 | 100 | 900 |

Figure 7:
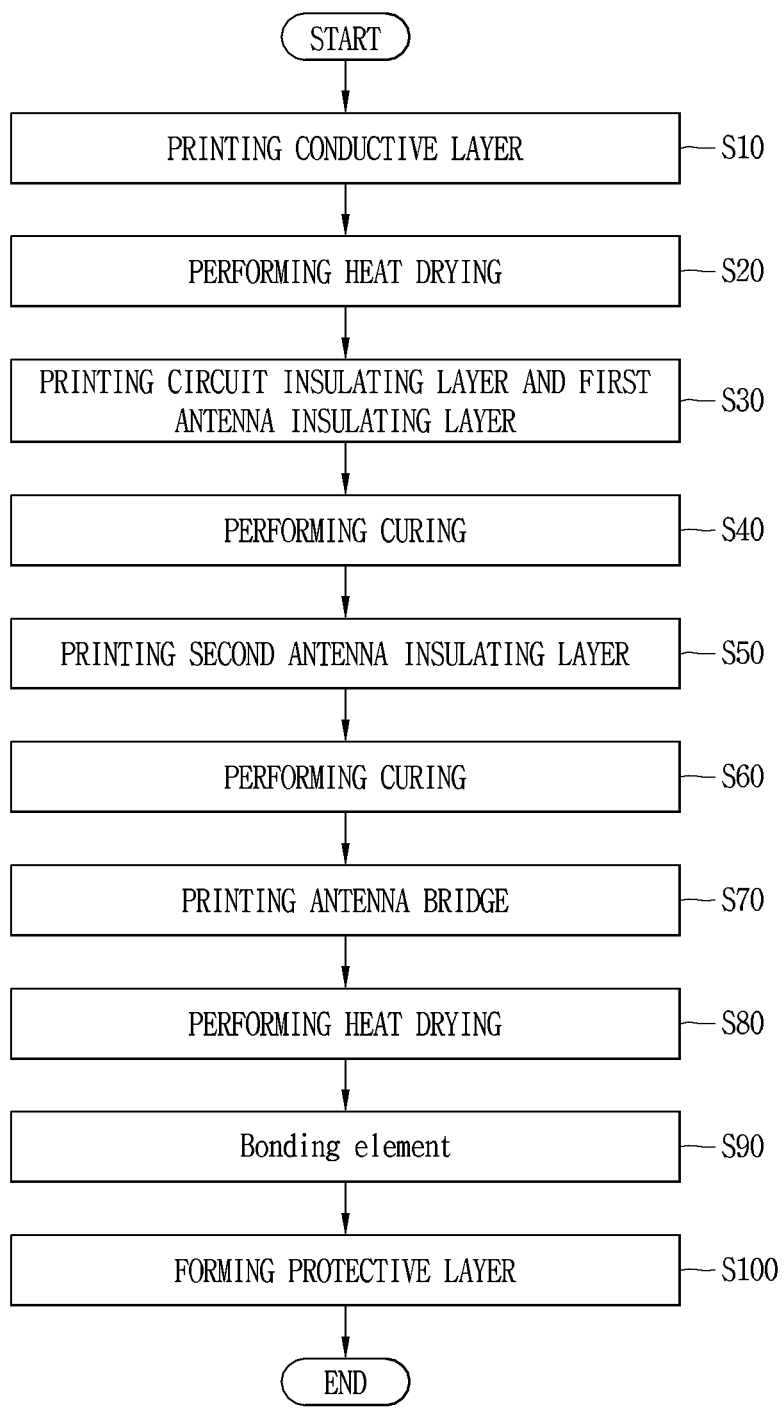
FIG. 7 is a flowchart of a method for manufacturing a sensor according to the present disclosure.

The steep slope of the graph represents a sensitive reaction to a small change in the concentration of sodium chloride, and this means a higher resolution. Referring to the graphs of FIGS. 7 and 8, the shorter the length of the sensing electrode exposed through the window, the narrower the width of the sensing electrode, and the wider the spacing between the two electrodes, the better the resolution. However, when the sensing electrode is designed solely for the purpose of improving resolution, problems on durability and reliability may occur. Therefore, the structure of the sensing electrode should be designed in consideration of resolution, durability, reliability, etc., and an appropriate structure of the sensing electrode has already been described above. FIG. 7 is a flowchart of a method for manufacturing a sensor according to the present disclosure, and FIGS. 8 to 11 are process views of a method for manufacturing the sensor of FIG. 7.

Referring to FIG. 7, the conductive layer is printed on the substrate through the printing process [S10].

The conductive layer includes the antenna pattern, the sensing electrode, and the circuit wiring. Accordingly, the antenna pattern, the sensing electrode, and the circuit wiring are simultaneously formed on the substrate through the process of printing the conductive layer on the substrate. In order to form the antenna pattern, the sensing electrode, and the circuit wiring simultaneously, the antenna pattern, the sensing electrode, and the circuit wiring should all be formed of a same material.

The advantages of the structure in which the antenna pattern 121, the sensing electrode 122, and the circuit wiring 123 are integrally formed, and are forming a single layer has already been described above.

The printing process of the conductive layer uses powder ink or paste. The powder ink or paste is composed of 40 to 70 weight percent of solid particles and 30 to 60 weight percent of organic matters containing solvent. With this composition, the problem of oxidation and corrosion of the sensing electrode can be solved.

The solid particle is at least one selected from silver (Ag), copper (Cu), and aluminum (Al). The solid particle has a spherical or flake shape.

The organic matter includes at least one selected from a group consisting of polyethylene oxide (PEO) series, oleic acid series, acrylate series, acetate series, and epoxy series.

The solvent includes at least one selected from a group consisting of acetone, allyl alcohol, acetic acid, acetol, methylalcohol, and benzene.

The process of printing the conductive layer may use any one method of screen printing, offset printing, and gravure printing, but is not limited thereto. In the present disclosure, any printing process capable of simultaneously forming the antenna pattern, the sensing electrode, and the circuit wiring may be used.

Figure 8:
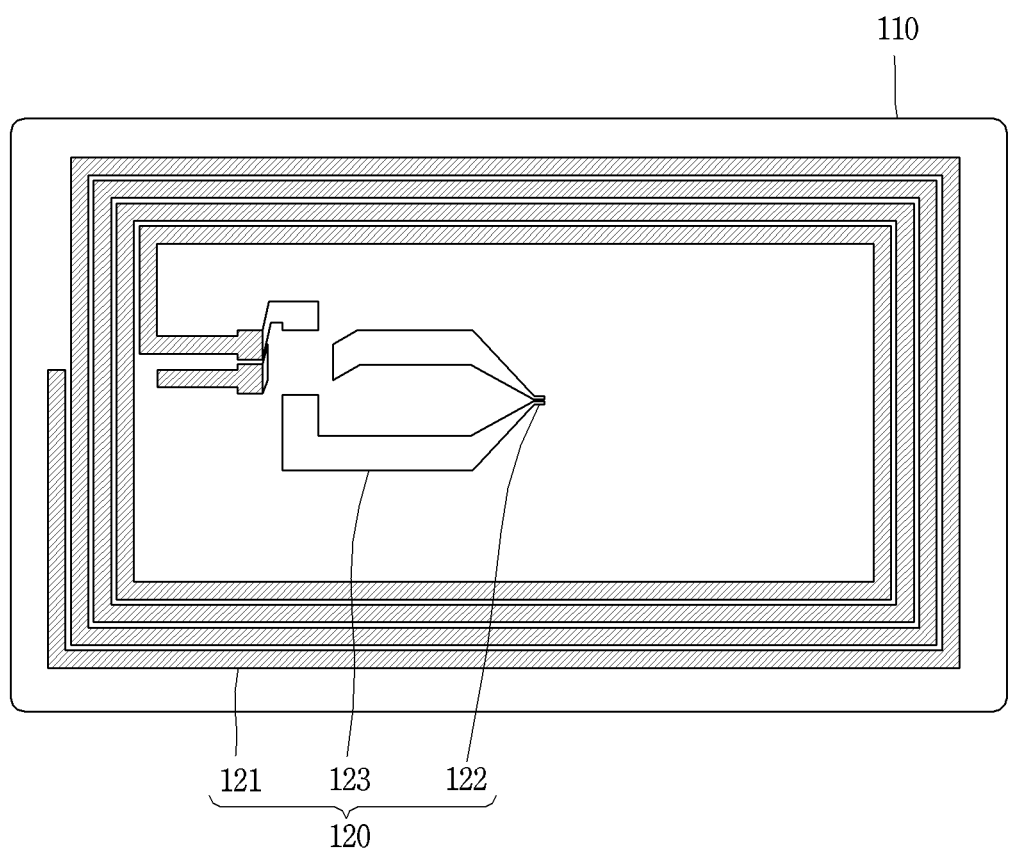
FIGS. 8 to 11 are process views of a method for manufacturing the sensor of FIG. 7.

FIG. 8 shows the substrate 110 and the conductive layer 120. Here, the conductive layer 120 is printed on the substrate 110.

Referring back to FIG. 7, the conductive layer is heat dried [S20] after the process of printing the conductive layer. Heat drying may be performed at 80-200° C. During the heat drying process, the solvent may be evaporated. A process error due to shrinkage that may occur in the heat drying process and the structure of the sensing electrode for solving the same have already been described.

In order to enable a low-temperature process at 200° C. or less, it is preferable that the solid particle has a size of several tens of nm to 20 µm in a form of powder.

Next, the circuit insulating layer and the first antenna insulating layer are printed [S30].

As the circuit insulating layer and the first antenna insulating layer are also formed of a same material, the circuit insulating layer and the first antenna insulating layer may also be simultaneously formed by a single printing process. The circuit insulating layer and the first antenna insulating layer form a same layer on the conductive layer.

Figure 9:
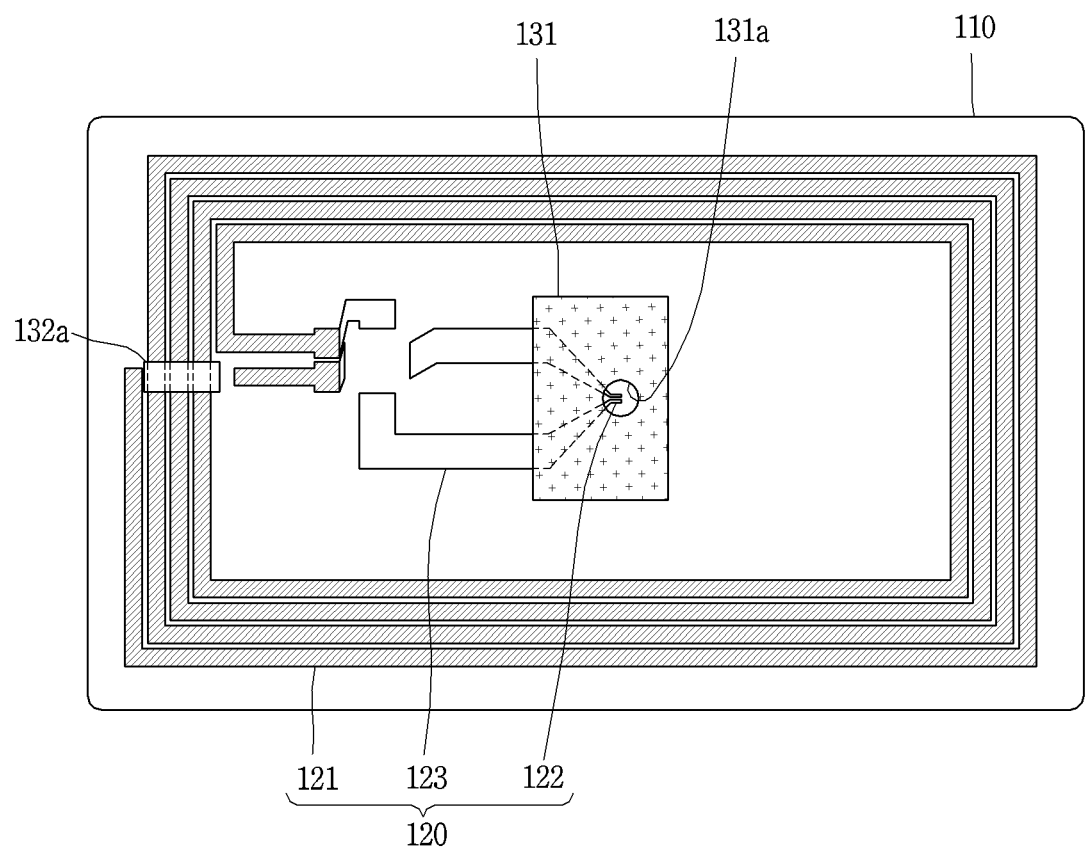

FIG. 9 shows the substrate 110, the conductive layer 120, the circuit insulating layer 131, and the first antenna insulating layer 132a. Here, the circuit insulating layer 131 and the first antenna insulating layer 132a are printed on the substrate 110 and the conductive layer 120.

Referring back to FIG. 7, the circuit insulating layer and the first antenna insulating layer are cured [S40]. Curing may be performed by ultraviolet (UV) light. Subsequently, the second antenna insulating layer is printed on the first antenna insulating layer [S50]. Then, the second antenna insulating layer is cured [S60]. Likewise, curing may be performed by ultraviolet (UV) light.

The second antenna insulating layer is for more reliable insulation. Therefore, when sufficient insulation is secured by the first antenna insulating layer, the process of printing the second antenna insulating layer and the process of curing the second antenna insulating layer may be omitted. On the contrary, when sufficient insulation is not secured by the first antenna insulating layer and the second antenna insulating layer, a process of printing and curing a third antenna insulating layer on the second antenna insulating layer may be added.

Figure 10:
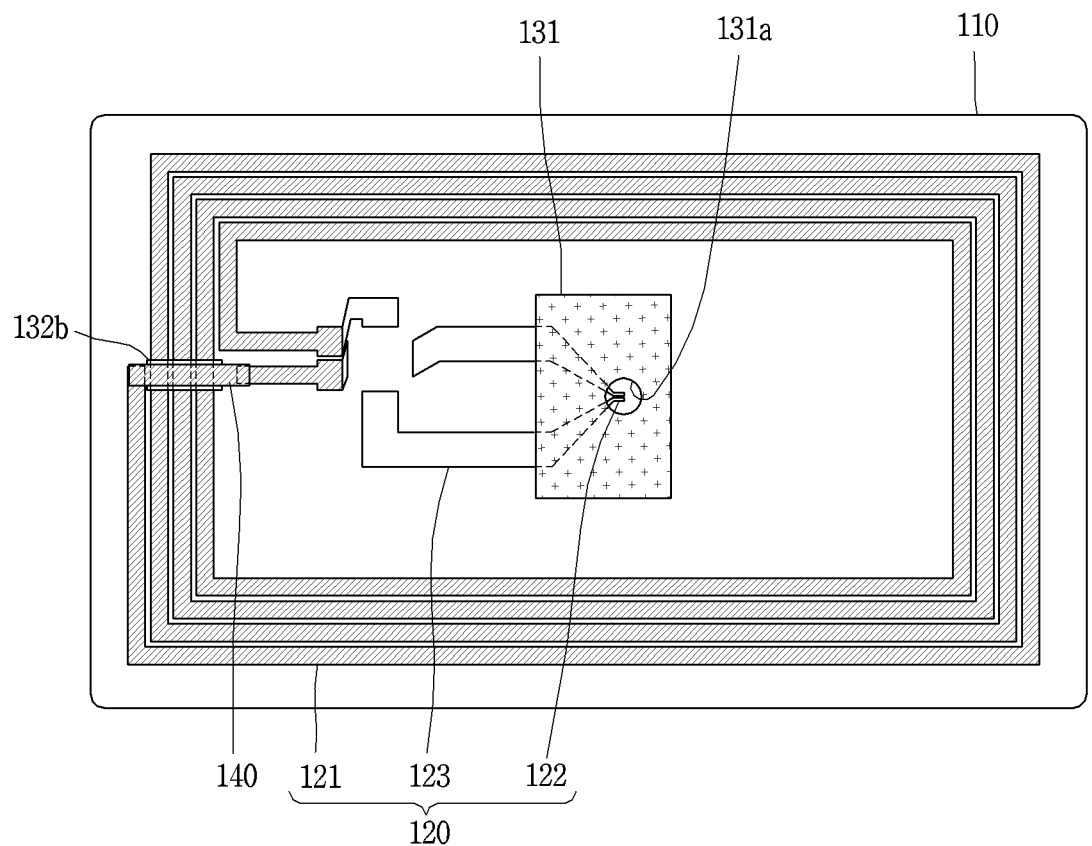

Next, the antenna bridge is printed on the second antenna insulating layer [S70]. The antenna bridge may be formed of a material same as that of the conductive layer. FIG. 10 shows the substrate 110, the conductive layer 120, the circuit insulating layer 131, the second antenna insulating layer 132*b*, and the antenna bridge 140. Here, the antenna bridge 140 is lastly printed.

Referring back to FIG. 7, the antenna bridge is heat dried [S80]. The process of heat drying the antenna bridge may be substantially the same as the process of heat drying the conductive layer.

Figure 11:
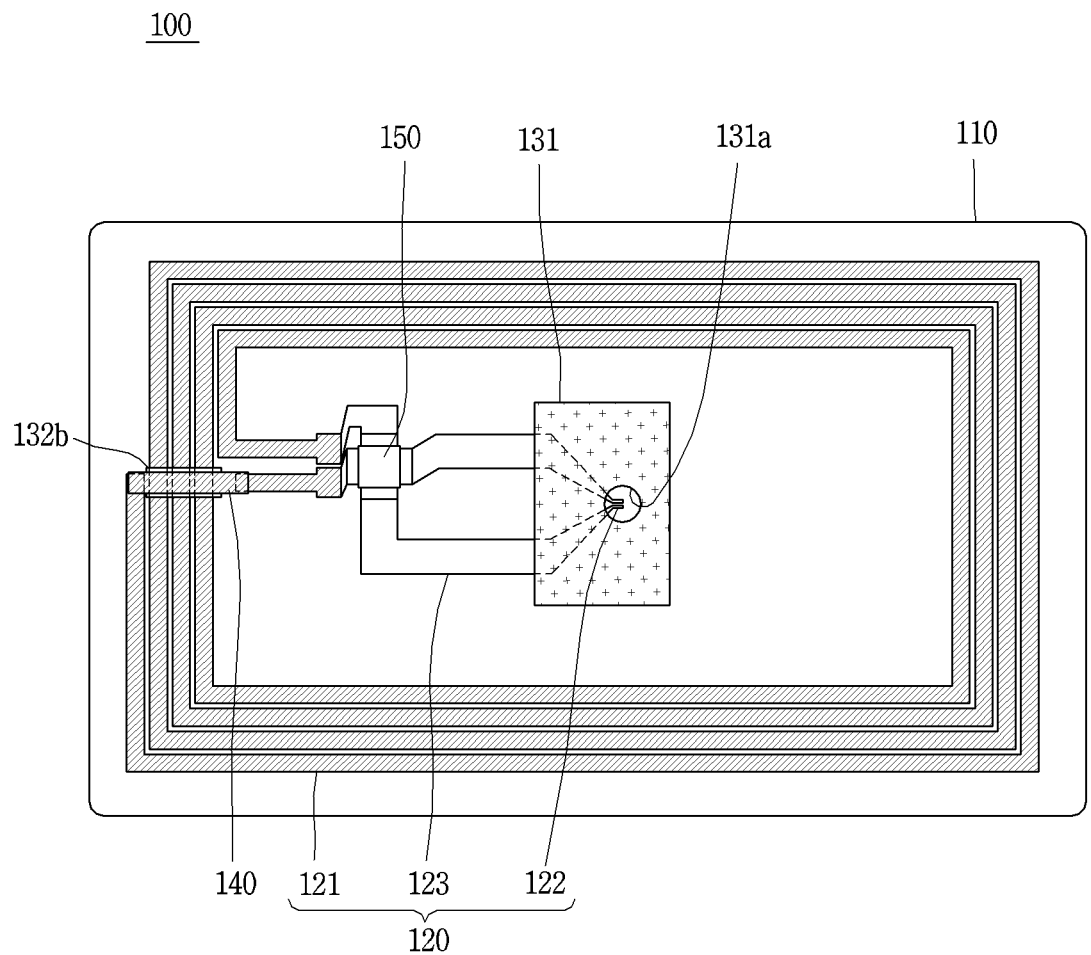

Next, the element is bonded to the substrate [S90]. The element allows an electric connection with the circuit wiring. FIG. 11 shows the sensor 100 on which the element 150 is bonded.

Finally, a protective layer covering all of the components of the sensor is formed [S100].

Figure 12:
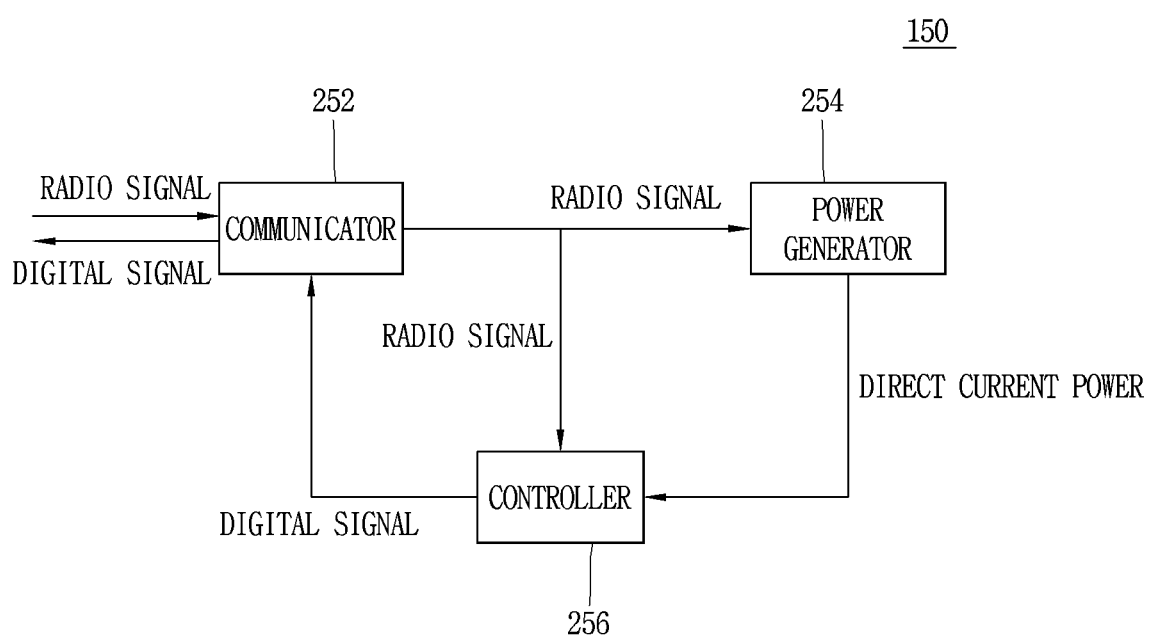
FIG. 12 is a control block diagram showing a control configuration of a sensor according to the present disclosure.

FIG. 12 is a control block diagram showing a control configuration of the sensor according to the present disclosure.

The element 150 included in the sensor 100 may include a communicator 252, a power generator 254, and a controller 256.

In an embodiment, the element 150 may electrically connect the antenna pattern 121 and the circuit wiring 123 through the antenna bridge 140.

The communicator 252 may receive a radio signal transmitted from an external device through the antenna pattern 121. In addition, the communicator 252 may transmit a digital signal transmitted to an external device through the antenna pattern 121.

Here, the communicator 252 may be, for example, a near field communication (NFC) module that performs near field communication, but is not limited thereto.

The power generator 254 may generate direct current power by harvesting energy from the radio signal received from the communicator 252. Here, the direct current power may be used as a driving power of the controller 256.

In addition, the power generator 254 may supply current or voltage to the sensing electrode 122 according to a control of the controller 256. Here, a magnitude (or level) of the current or the voltage may be varied by the controller 256, but is not limited thereto.

The controller 256 is woken up by the direct current power inputted from the power generator 254 and may analyze the radio signal.

A case where the radio signal is analyzed as a signal requesting measurement of ion concentration of water quality of a sensing target material will be described first as follows.

The controller 256 may control the power generator 254 so that alternating current power, that is, driving voltage is applied to the sensing electrode 122 and therefore a first driving current is supplied to the sensing electrode 122.

Thereafter, the controller 256 may determine whether a first measurement voltage corresponding to a change in the first driving current measured by the sensing electrode 122 satisfies a set first ion reference voltage.

When the first measurement voltage satisfies the first ion reference voltage, the controller 256 may generate a first digital signal corresponding to ion concentration calculated by applying the first measurement voltage to a set first logarithmic function so as to transmit the first digital signal to an external device.

The first logarithmic function is as shown in [Equation 1] below.

$$Y = e^{\left(\frac{ln(49.204/x)}{0.915}\right)}$$ [Equation 1]

Here, Y may be ion concentration and x may be first measurement voltage.

Here, the first driving current may be from 10 μA to 14 μA. This is a current value that makes it easy to check ion concentration contained in the sensing target material. However, when the first driving current is less than 10 μA, changes are small due to ion concentration of the sensing target material. And, when the first driving current is greater than 14 μA, it is easy to measure ion concentration of the sensing target material, but a result for ion concentration is not significantly different from the case in which the first driving current is 14 μA, and therefore, an effect thereof may not occur.

Here, when the first measurement voltage does not satisfy the first ion reference voltage, the controller 256 supplies a second driving current lower than the first driving current to the sensing electrode 122 to thereby determine whether the second measurement voltage sensed at the sensing electrode 122 satisfies a set second ion reference voltage.

When the second measurement voltage satisfies the second ion reference voltage, the controller 256 may generate a second digital signal corresponding to ion concentration calculated by applying the second measurement voltage to a second logarithmic function that is different from the set first logarithmic function so as to transmit the second digital signal to an external device.

The second logarithmic function is as shown in [Equation 2] below.

$$Y = e^{\left(\frac{ln(3.8894/x)}{0.728}\right)}$$ [Equation 2]

Here, Y may be the ion concentration and x may be second measurement voltage.

Here, the second driving current may be from 1 μA to 3 μA. This is a current value that makes it easy to check ion concentration contained in the sensing target material. However, when the second driving current is greater than 3 μA, it is easy to measure ion concentration of the sensing target material, but a result for ion concentration is not significantly different from the case in which the second driving current is 3 μA, and therefore, an effect thereof may not occur.

In addition, when the second measurement voltage does not satisfy the second ion reference voltage, the controller 256 may generate a third digital signal corresponding to ion concentration calculated by applying the second measurement voltage to a set primary single equation so as to transmit the third digital signal to an external device.

The primary single equation is as shown in [Equation 3] below.

$$Y = \left(\frac{1.1114 - x}{0.0244}\right) \quad \text{[Equation 3]}$$

Here, Y may be ion concentration and x may be measurement voltage.

A case where the radio signal is a signal requesting measurement of salinity of the sensing target material, which is different from the above, will be described first as follows.

The controller 256 may control the power generator 254 so that alternating current power, that is, driving voltage is supplied to the sensing electrode 122.

Here, since the measurement of salinity of the sensing target material shows different results depending on a temperature, the measurement is preferably performed when the temperature of the sensing target material is maintained at room temperature (e.g., 22° C.).

When a predetermined time has passed after the driving voltage is supplied, the controller 256 may determine whether the first sampling voltage obtained by sampling the third measurement voltage sensed at the sensing electrode 122 according to the sampling cycle falls within either a range of a set first sampling voltage value or a range of a second sampling voltage value greater than the first sampling voltage value.

In an embodiment, the predetermined time may be a time maintained at room temperature even if the temperature of the sensing target material is high or low.

When it is determined that the first sampling voltage falls within the range of the second sampling voltage value, the controller 256 may generate a fourth digital signal corresponding to salinity calculated by applying the first sampling voltage to the set primary single equation so as to transmit the fourth digital signal to an external device.

The primary single equation is as shown in [Equation 4] below.

$$Y = \left(\frac{3886.2 - x}{1661.8}\right) \quad \text{[Equation 4]}$$

Y may be salinity and x may be first sampling voltage.

In addition, when it is determined that the first sampling voltage falls within a range of a first temperature sampling voltage value, the controller 256 may re-supply the driving current to the sensing electrode 122 to determine whether the second sampling voltage obtained by sampling the fourth measurement voltage sensed at the sensing electrode 122 according to the sampling cycle falls within the range of the first temperature sampling voltage value.

When it is determined that the second sampling voltage falls within the range of the first sampling voltage value, the controller 256 may generate a fifth digital signal corresponding to salinity by applying the second sampling voltage to a set third logarithmic function so as to transmit the fifth digital signal to an external device.

The third logarithmic function is as shown in [Equation 5] below.

$$Y = e^{\left(\frac{2784.5 - x}{494.5}\right)} \quad \text{[Equation 5]}$$

Here, Y may be ion concentration and x may be second sampling voltage.

Here, when it is determined that the second sampling voltage does not fall within the range of the first sampling voltage value, the controller 256 may determine that the second sampling voltage falls within the range of the second sampling voltage value, and generate a sixth digital signal corresponding to salinity calculated by applying the second sampling voltage to the primary single equation so as to transmit the sixth digital signal to an external device.

A case where the radio signal is determined to be a signal requesting measurement of salinity of the sensing target material and including the temperature of the sensing target material, which is different from the above, will be described first as follows.

First, the controller 256 may determine whether the temperature of the sensing target material falls within either a first temperature range or a second temperature range.

In an embodiment, the first temperature range may be lower than room temperature, and the second temperature range may be higher than room temperature.

For example, the first temperature range may be −10° C. to 0° C., the second temperature range may be 50° C. to 60° C., and temperature between the first temperature range and the second temperature range may be determined as room temperature, but not limited thereto.

When it is determined that the temperature of the sensing target material falls within the first temperature range, the controller 256 may control the power generator 254 to supply driving voltage to the sensing electrode 122.

The controller 256 may determine whether the third sampling voltage obtained by sampling the fifth measurement voltage sensed at the sensing electrode 122 according to the sampling cycle falls within either a range of a set first temperature sampling voltage value or a range of a second temperature sampling voltage value greater than the first temperature sampling voltage value.

When it is determined that the third sampling voltage falls within the range of the second sampling voltage value, the controller 256 may generate a seventh digital signal corresponding to salinity calculated by applying the third sampling voltage to the set primary single equation so as to transmit the seventh digital signal to an external device.

The primary single equation is as shown in [Equation 6] below.

$$Y = \left(\frac{39119.9 - x}{1231.3}\right) \quad \text{[Equation 6]}$$

Y may be salinity and x may be third sampling voltage.

In addition, when it is determined that the third sampling voltage falls within the range of the first temperature sampling voltage value, the controller 256 may re-supply the driving current to the sensing electrode 122 to determine whether the fourth sampling voltage obtained by sampling the sixth measurement voltage sensed at the sensing electrode 122 according to the sampling cycle falls within the range of the first temperature sampling voltage value.

When it is determined that the fourth sampling voltage falls within the range of the first temperature sampling voltage value, the controller 256 may generate an eighth digital signal corresponding to salinity by applying the fourth sampling voltage to a set fourth logarithmic function so as to transmit the eighth digital signal to an external device.

The fourth logarithmic function is as shown in [Equation 7] below.

$$Y = e^{\left(\frac{2975.8-x}{515.5}\right)} \quad \text{[Equation 7]}$$

Here, Y may be ion concentration and x may be fourth sampling voltage.

Here, when it is determined that the fourth sampling voltage does not fall within the range of the first temperature sampling voltage value, the controller 256 may determine that the fourth sampling voltage falls within the range of the second temperature sampling voltage value, and generate a ninth digital signal corresponding to salinity calculated by applying the fourth sampling voltage to the primary single equation so as to transmit the ninth digital signal to an external device.

When it is determined that the temperature of the sensing target material falls within the second temperature range, the controller 256 may control the power generator 254 to supply driving voltage to the sensing electrode 122.

The controller 256 may determine whether the fifth sampling voltage obtained by sampling the seventh measurement voltage sensed at the sensing electrode 122 according to the sampling cycle falls within either a range of a set third temperature sampling voltage value or a range of a fourth temperature sampling voltage value greater than the third temperature sampling voltage value.

When it is determined that the fifth sampling voltage falls within the range of the fourth sampling voltage value, the controller 256 may generate a tenth digital signal corresponding to salinity calculated by applying the fifth sampling voltage to a set fifth logarithmic function so as to transmit the tenth digital signal to an external device.

The fifth logarithmic function is as shown in [Equation 8] below.

$$Y = e^{\left(\frac{2734.2-x}{338.5}\right)} \quad \text{[Equation 8]}$$

Y may be salinity and x may be fifth sampling voltage.

In addition, when it is determined that the fifth sampling voltage falls within the range of the third temperature sampling voltage value, the controller 256 may re-supply the driving current to the sensing electrode 122 to determine whether the sixth sampling voltage obtained by sampling the eighth measurement voltage sensed at the sensing electrode 122 according to the sampling cycle falls within the range of the third temperature sampling voltage value.

When it is determined that the sixth sampling voltage falls within the range of the third temperature sampling voltage value, the controller 256 may generate an eleventh digital signal corresponding to salinity by applying the sixth sampling voltage to a set sixth logarithmic function so as to transmit the eleventh digital signal to an external device.

The sixth logarithmic function is as shown in [Equation 9] below.

$$Y = e^{\left(\frac{2556-x}{485.6}\right)} \quad \text{[Equation 9]}$$

Here, Y may be ion concentration and x may be sixth sampling voltage.

Here, when it is determined that the sixth sampling voltage does not fall within the range of the third temperature sampling voltage value, the controller 256 may determine that the sixth sampling voltage falls within the range of the fourth temperature sampling voltage value, and generate a twelfth digital signal corresponding to salinity calculated by applying the sixth sampling voltage to the fifth logarithmic function so as to transmit the twelfth digital signal to an external device.

FIGS. 13 to 16 are flowcharts of a method for operating the sensor according to the present disclosure.

Figure 13:
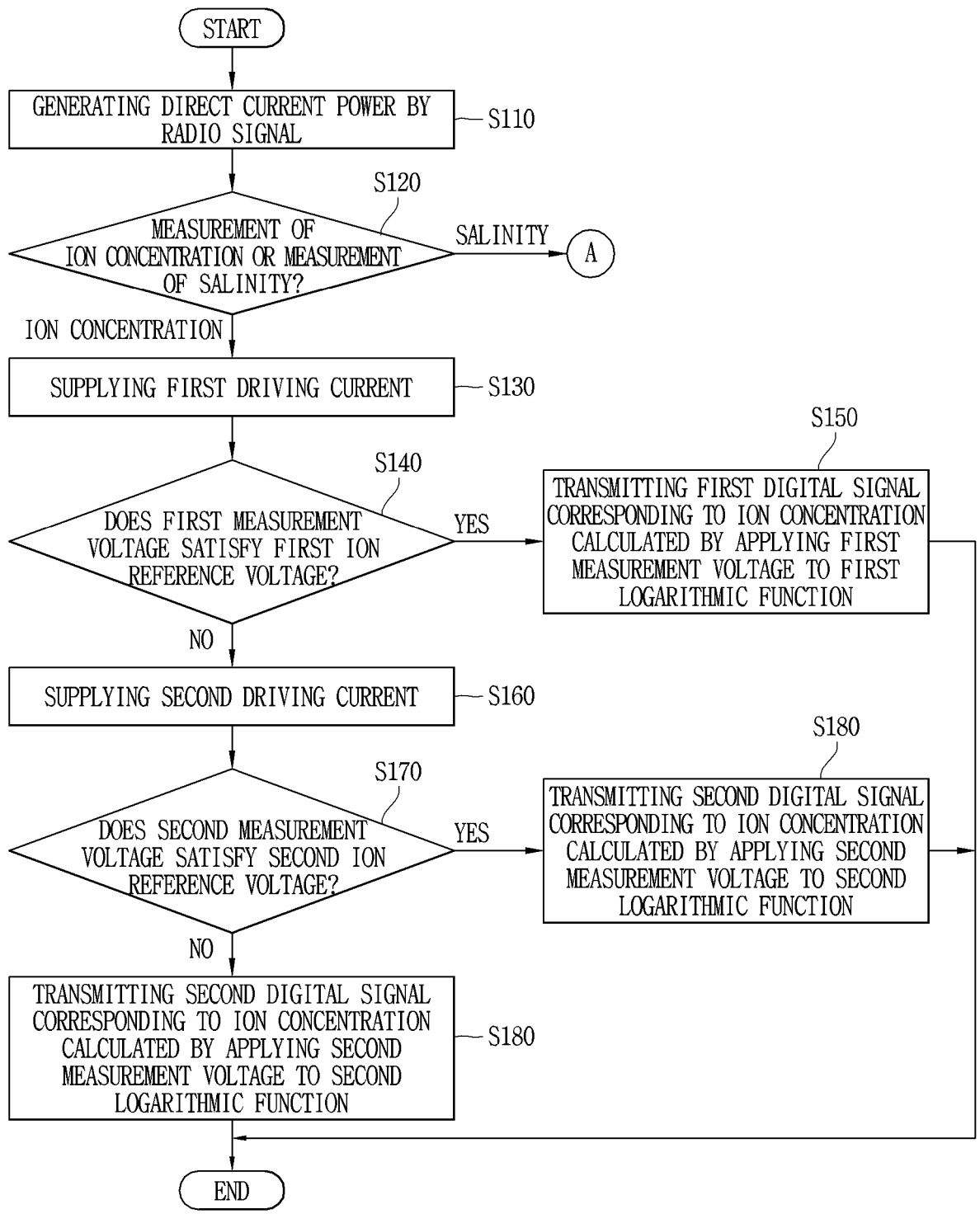
FIGS. 13 to 16 are flowcharts of a method for operating a sensor according to the present disclosure.

First, referring to FIG. 13, when the element 150 included in the sensor 100 receives a radio signal from an external device, direct current power may be generated by the radio signal [S110].

In other words, the power generator 252 included in the element 150 may generate direct current power by harvesting energy from the radio signal.

Here, the element 150 may be woken up by direct current power to determine whether the radio signal is a signal requesting measurement of ion concentration of water quality of a sensing target material or requesting a measurement of salinity of the sensing target material [S120].

When the radio signal is determined to be the signal requesting measurement of ion concentration [S120], the element 150 may supply the first driving current to the first electrode 122*a* and the second electrode 122*b* so as to sense the first measurement voltage corresponding to the impedance change between the first electrode 122*a* and the second electrode 122*b* included in the sensing electrode 122 to which the sensing target material is brought into contact with [S130].

The element 150 may determine whether a first measurement voltage corresponding to a change in the first driving current measured by the first electrode 122*a* and the second electrode 122*b* satisfies a set first ion reference voltage [S140].

When the first measurement voltage satisfies the first ion reference voltage [S140], the element 150 may transmit the first digital signal corresponding to ion concentration calculated by applying the first measurement voltage to the first logarithmic function to an external device [S150].

In other words, the element 150 may calculate ion concentration of the sensing target material by applying the first measurement voltage to the first logarithmic function of [Equation 1] to generate the first digital signal corresponding to the ion concentration.

A detailed description has been described with reference to FIG. 12 and will not be repeated.

When the first measurement voltage does not satisfy the first ion reference voltage [S140], the element 150 may supply a second driving current lower than the first driving current to the first electrode 122*a* and the second electrode 122*b* [S160].

Thereafter, the element 150 may determine whether the second measurement voltage sensed at the first electrode 122*a* and the second electrode 122*b* by the second driving current satisfies the set second ion reference voltage [S170].

When the second measurement voltage satisfies the second ion reference voltage [S170], the element 150 may transmit the second digital signal corresponding to ion concentration calculated by applying the second measurement voltage to the second logarithmic function to an external device [S180].

In other words, the element 150 may calculate ion concentration of the sensing target material by applying the second measurement voltage to the second logarithmic function of [Equation 2] to generate the second digital signal corresponding to the ion concentration.

A detailed description has been described with reference to FIG. 12 and will not be repeated.

When the second measurement voltage does not satisfy the second ion reference voltage [S170], the element 150 may generate a third digital signal corresponding to ion concentration calculated by applying the second measurement voltage to a set primary single equation so as to transmit the third digital signal to an external device [S190].

In other words, the element 150 may calculate ion concentration of the sensing target material by applying the third measurement voltage to the primary single equation of [Equation 3] to generate the third digital signal corresponding to the ion concentration.

A detailed description has been described with reference to FIG. 12 and will not be repeated.

Figure 14:
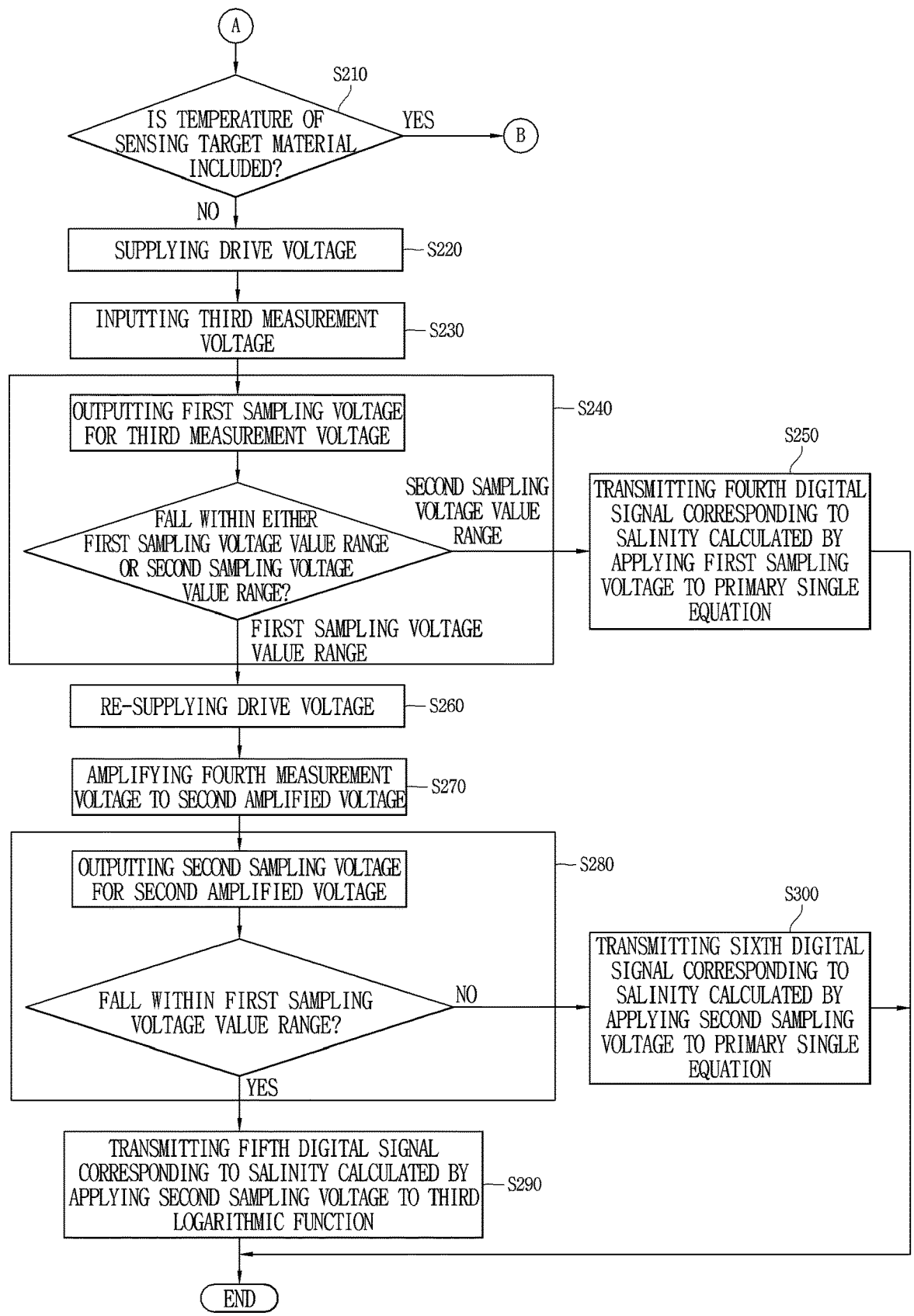

Referring to FIG. 14, when the radio signal is determined to be the signal requesting measurement of salinity, the element 150 may determine whether the temperature of the sensing target material is included in the radio signal [S210].

When the radio signal does not include the temperature of the sensing target material [S210], the element 150 may supply the driving current to the first electrode 122a and the second electrode 122b so as to sense the third measurement voltage corresponding to the impedance change between the first electrode 122a and the second electrode 122b to which the sensing target material is brought into contact with [S220].

After supplying the driving voltage for a predetermined time, the element 150 may receive the third measurement voltage sensed by the first electrode 122a and the second electrode 122b [S230].

That is, since the measurement of salinity of the sensing target material shows different results depending on the temperature, the element 150 may measure the third measurement voltage when the temperature of the sensing target material decreases or increases to be maintained at room temperature (e.g., 22° C.).

Thereafter, the element 150 may determine whether the first sampling voltage obtained by sampling the third measurement voltage according to the sampling cycle falls within either a range of a set first sampling voltage value or a range of a second sampling voltage value greater than the first sampling voltage value [S240].

When it is determined that the first sampling voltage falls within the range of the second sampling voltage value, the element 150 may generate a fourth digital signal corresponding to salinity calculated by applying the first sampling voltage to the set primary single equation so as to transmit the fourth digital signal to an external device [S250].

In other words, the element 150 may calculate salinity of the sensing target material by applying the first sampling voltage to the primary single equation of [Equation 4] to generate the fourth digital signal corresponding to the salinity.

When it is determined that the first sampling voltage falls within the range of the first sampling voltage value [S240], the element 150 may re-supply the driving voltage to the first electrode 122a and the second electrode 122b [S260] to receive the fourth measurement voltage sensed at the first electrode 122a and the second electrode 122b [S270].

The element 150 may re-determine whether the second sampling voltage obtained by sampling the fourth measurement voltage according to the sampling cycle falls within the range of the first sampling voltage value [S280].

When it is determined that the second sampling voltage falls within the range of the first sampling voltage value [S280], the element 150 may generate a fifth digital signal corresponding to salinity by applying the second sampling voltage to a set third logarithmic function so as to transmit the fifth digital signal to an external device [S290].

In other words, the element 150 may calculate salinity of the sensing target material by applying the second sampling voltage to the third logarithmic function of [Equation 5] to generate the fifth digital signal corresponding to the salinity.

When it is determined that the second sampling voltage does not fall within the range of the first sampling voltage value [S280], the element 150 may determine that the second sampling voltage falls within the range of the second sampling voltage value, and generate a sixth digital signal corresponding to salinity by applying the second sampling voltage to the primary single equation so as to transmit the sixth digital signal to an external device [S300].

In other words, the element 150 may calculate salinity of the sensing target material by applying the second sampling voltage to the primary single equation of [Equation 4] to generate the sixth digital signal corresponding to the salinity.

A detailed description has been described with reference to FIG. 12 and will not be repeated.

Figure 15:
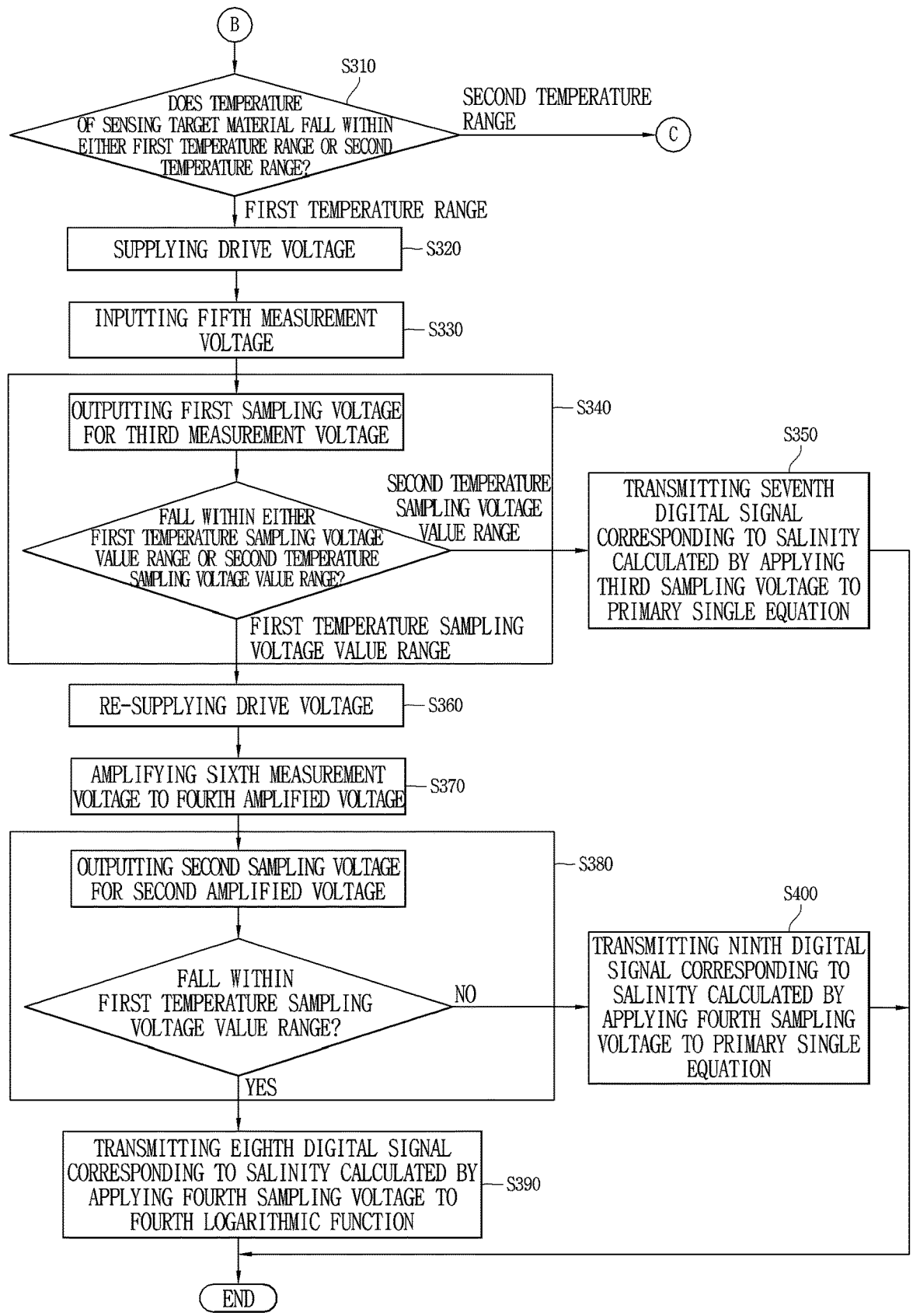

Referring to FIG. 15, when the radio signal includes the temperature of the sensing target material [S210], the element 150 may determine whether the temperature of the sensing target material falls within either the first temperature range or the second temperature range [S310].

In an embodiment, the first temperature range may be lower than room temperature, for example −10° C. to 0° C., the second temperature range may be a temperature range higher than room temperature, for example 50° C. to 60° C., and a temperature between the first temperature range and the second temperature range may be determined as room temperature.

When it is determined that the temperature of the sensing target material falls within the first temperature range [S310], the element 150 may supply the driving current to the first electrode 122a and the second electrode 122b so as to sense the fifth measurement voltage corresponding to the impedance change between the first electrode 122a and the second electrode 122b to which the sensing target material is brought into contact with [S320].

The element 150 may receive the fifth measurement voltage sensed by the first electrode 122a and the second electrode 122b [S330].

Thereafter, the element 150 may determine whether the third sampling voltage obtained by sampling the third measurement voltage according to the sampling cycle falls within either the range of the set first temperature sampling voltage value or the range of the second temperature sampling voltage value greater than the first temperature sampling voltage value [S340].

When it is determined that the third sampling voltage falls within the range of the second temperature sampling voltage value [S340], the element 150 may generate a seventh digital signal corresponding to salinity calculated by applying the third sampling voltage to the set primary single equation so as to transmit the seventh digital signal to an external device [S350].

In other words, the element 150 may calculate salinity of the sensing target material by applying the third sampling voltage to the primary single equation of [Equation 6] to generate the seventh digital signal corresponding to the salinity.

When it is determined that the third sampling voltage falls within the range of the first temperature sampling voltage value [S340], the element 150 may re-supply the driving voltage to the first electrode 122a and the second electrode 122b [S360] to receive the sixth measurement voltage sensed at the first electrode 122a and the second electrode 122b [S370].

The element 150 may re-determine whether the fourth sampling voltage obtained by sampling the sixth measurement voltage according to the sampling cycle falls within the range of the first temperature sampling voltage value [S380].

When it is determined that the fourth sampling voltage falls within the range of the first sampling voltage value [S380], the element 150 may generate the eighth digital signal corresponding to salinity by applying the fourth sampling voltage to the set fourth logarithmic function so as to transmit the eighth digital signal to an external device [S390].

In other words, the element 150 may calculate salinity of the sensing target material by applying the fourth sampling voltage to the fourth logarithmic function of [Equation 7] to generate the eighth digital signal corresponding to the salinity.

When it is determined that the fourth sampling voltage does not fall within the range of the first temperature sampling voltage value [S380], the element 150 may determine that the fourth sampling voltage falls within the range of the second sampling voltage value, and generate a ninth digital signal corresponding to salinity by applying the fourth sampling voltage to the primary single equation so as to transmit the ninth digital signal to an external device [S400].

In other words, the element 150 may calculate salinity of the sensing target material by applying the fourth sampling voltage to the primary single equation of [Equation 6] to generate the ninth digital signal corresponding to the salinity.

A detailed description has been described with reference to FIG. 12 and will not be repeated.

Figure 16:
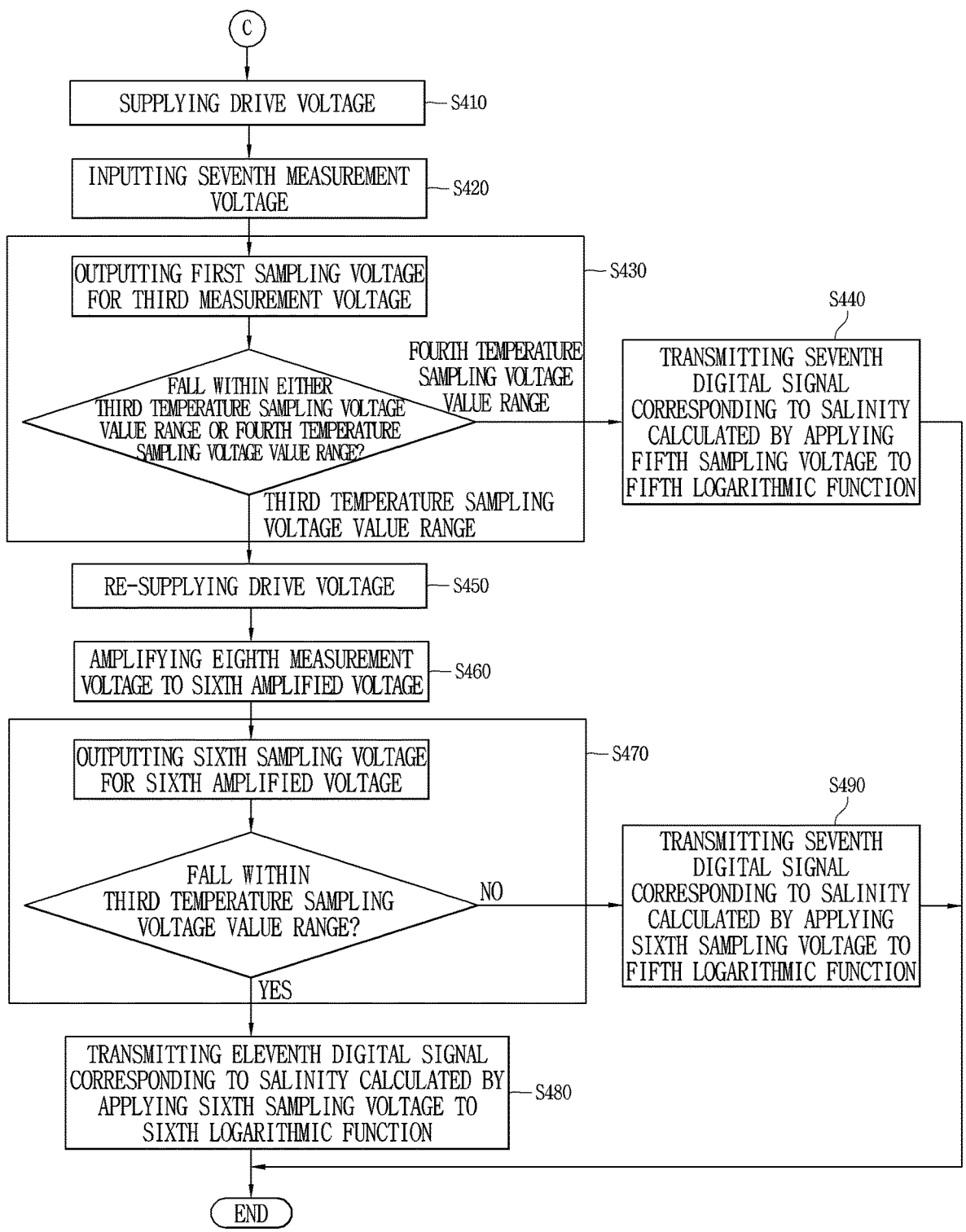

Referring to FIG. 16, when it is determined that the temperature of the sensing target material falls within the second temperature range [S310], the element 150 may supply the driving current to the first electrode 122a and the second electrode 122b so as to sense the seventh measurement voltage corresponding to the impedance change between the first electrode 122a and the second electrode 122b to which the sensing target material is brought into contact with [S410].

The element 150 may receive the seventh measurement voltage sensed by the first electrode 122a and the second electrode 122b [S420].

Thereafter, the element 150 may determine whether the fifth sampling voltage obtained by sampling the seventh measurement voltage according to the sampling cycle falls within either the range of the set third temperature sampling voltage value or the range of the fourth temperature sampling voltage value greater than the third temperature sampling voltage value [S430].

When it is determined that the fifth sampling voltage falls within the range of the fourth temperature sampling voltage value [S430], the element 150 may generate the tenth digital signal corresponding to salinity calculated by applying the fifth sampling voltage to the set fifth logarithmic function so as to transmit the tenth digital signal to an external device [S440].

In other words, the element 150 may calculate salinity of the sensing target material by applying the fifth sampling voltage to the fifth logarithmic function of [Equation 8] to generate the tenth digital signal corresponding to the salinity.

When it is determined that the fifth sampling voltage falls within the range of the third temperature sampling voltage value [S430], the element 150 may re-supply the driving voltage to the first electrode 122a and the second electrode 122b [S450] to receive the eighth measurement voltage sensed at the first electrode 122a and the second electrode 122b [S460].

The element 150 may re-determine whether the sixth sampling voltage obtained by sampling the eighth measurement voltage according to the sampling cycle falls within the range of the third temperature sampling voltage value [S470].

When it is determined that the sixth sampling voltage falls within the range of the third sampling voltage value [S470], the element 150 may generate the eleventh digital signal corresponding to salinity by applying the sixth sampling voltage to the set sixth logarithmic function so as to transmit the eleventh digital signal to an external device [S480].

In other words, the element 150 may calculate salinity of the sensing target material by applying the sixth sampling voltage to the sixth logarithmic function of [Equation 9] to generate the eleventh digital signal corresponding to the salinity.

When it is determined that the sixth sampling voltage does not fall within the range of the third temperature sampling voltage value [S470], the element 150 may determine that the sixth sampling voltage falls within the range of the fourth sampling voltage value, and generate the twelfth digital signal corresponding to salinity by applying the sixth sampling voltage to the fifth logarithmic function so as to transmit the twelfth digital signal to an external device [S490].

In other words, the element 150 may calculate salinity of the sensing target material by applying the sixth sampling voltage to the fifth logarithmic function of [Equation 8] to generate the twelfth digital signal corresponding to the salinity.

A detailed description has been described with reference to FIG. 12 and will not be repeated.

Figure 17:
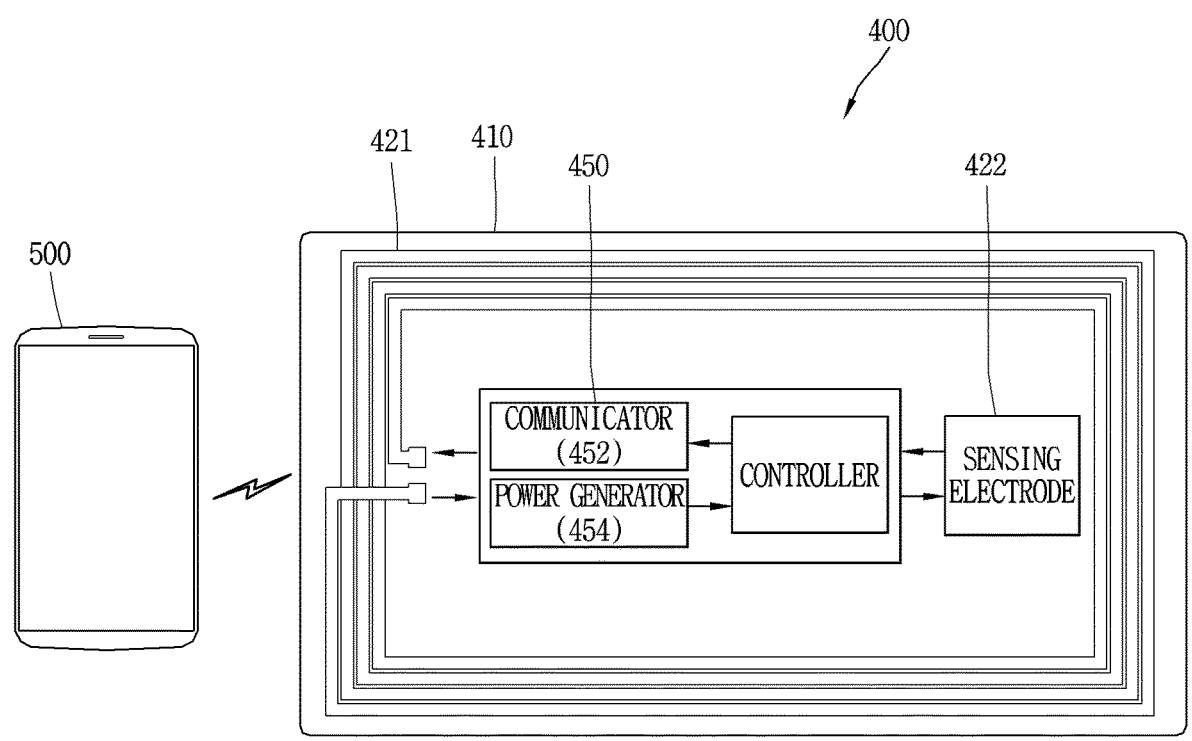
FIG. 17 is a conceptual view of a linked operation between a sensor and an external device according to the present disclosure.

FIG. 17 is a conceptual view of a linked operation between a sensor and an external device according to the present disclosure.

Referring to FIG. 17, a sensor 400 may transmit and receive a radio signal to and from an external device 500.

First, the sensor 400 may include a substrate 410, an antenna pattern 421, a sensing electrode 422, and an element 450.

In an embodiment, the sensor 400 has a configuration same as that of the sensor 100 shown in FIGS. 1 to 4, and a detailed description thereof will not be repeated.

The element 450 may include a communicator 452, a power generator 454, and a controller 456.

In an embodiment, the controller 456 may include an analog-to-digital converter that converts an analog signal into a digital signal, but is not limited thereto.

A detailed description of the element 450 has been described in FIGS. 1 to 4 and will not be repeated.

The external device 500 includes a mobile terminal having a wireless communication function and a display.

First, the communicator 452 may receive a radio signal from the external device 500 through the antenna pattern 410.

Here, the power generator 454 may be, for example, a rectifier circuit of an NFC Tag IC, and may generate direct current power by harvesting energy from a radio signal.

As such, the sensor 400 does not have a configuration for supplying power by itself but generates direct current power by using a radio signal received from an external device, and the generated direct current power operates the communicator 452, the power generator 454, the controller 456, and the sensing electrode 422.

The controller 456 is operated by receiving direct current power. The controller 456 may generate alternating current power (e.g., 10 KHz, 1.2 V) and input the alternating current power to the sensing electrode 422.

When the sensing electrode 422 reacts to the sensing target material, the sensing electrode 422 causes an impedance change. And, the impedance change of the sensing electrode 422 represents a change in alternating current power generated by the controller 456 as a measurement voltage. The sensing target material may be classified according to a range of an output value.

The measurement voltage is converted into a digital signal. The controller 456 converts a change in alternating voltage due to a change in impedance of the sensing electrode 422 into a digital signal.

Thereafter, the communicator 454 (e.g., NFC Tag IC) transmits the digital signal to the external device 500 through the antenna pattern 421.

The external device 500 generates, stores, and manages information by receiving the digital signal from the sensor 400. In addition, the external device 500 may display information through the display.

As described above, since the sensor 400 is not provided with a power source but is able to communicate with the external device 500, the sensor 400 may not have a display or the like. This may eventually contribute to miniaturization and enhancement of portability of the sensor 400 to thereby reduce the manufacturing cost of the sensor 400.

Features, structures, effects, etc. described in the embodiments above are included in at least one embodiment of the present disclosure, and are not necessarily limited to only one embodiment. Further, the features, structures, effects, etc. illustrated in each embodiment may be combined or modified for other embodiments by those skilled in the art to which the embodiments belong. Accordingly, contents related to such combinations and modifications should be construed as being included in the scope of the present disclosure.

In addition, although the foregoing description has been given with reference to the embodiments, these are merely illustrative and do not limit the present disclosure, and it will be understood that those skilled in the art will be able to variously modify and change the present disclosure without departing from the essential characteristics of the embodiments. For example, each component specifically shown in the embodiments can be modified. And differences related to these modifications and applications should be construed as being included in the scope of the present disclosure defined in the appended claims.

The invention claimed is:

1. A sensor comprising:
a substrate;
an antenna pattern formed in a spiral shape on the substrate;
a first electrode and a second electrode formed on the substrate and spaced apart from each other in parallel;
a circuit wiring formed to be connected to each of the first electrode and the second electrode;
an element bonded to the antenna pattern and the circuit wiring; and
a circuit insulating layer disposed on at least a portion of the circuit wiring and having a window to expose the first electrode and the second electrode,
wherein cross sections of the first electrode and the second electrode each has a curvature.

2. The sensor of claim 1, wherein the first electrode and the second electrode each forms an acute contact angle with the substrate.

3. The sensor of claim 1, wherein the first electrode and the second electrode each has a width of 50 μm to 200 μm.

4. The sensor of claim 1, wherein a distance between the first electrode and the second electrode is from 900 μm to 1,500 μm.

5. The sensor of claim 1, wherein a thickness of each of the first electrode and the second electrode is from 900 μm to 1,500 μm.

6. The sensor of claim 1, wherein a thickness of the circuit insulating layer is thicker than the first electrode and the second electrode, and is from 800 nm to 30 μm.

7. The sensor of claim 1, wherein the first electrode and the second electrode each comprises a first end portion, a second end portion, and a central portion between the first end portion and the second end portion in a lengthwise direction, and
wherein the window exposes the central portion.

8. The sensor of claim 7, wherein a length of the central portion is from 500 μm to 2,000 μm.

9. The sensor of claim 1, further comprising:
an antenna insulating layer in which a material and a thickness thereof are identical to those of the circuit insulating layer, and disposed on at least a portion of the antenna pattern; and
an antenna bridge disposed on the antenna insulating layer, connecting two portions of the antenna pattern to each other, and connecting the antenna pattern and the circuit wiring to each other.

10. The sensor of claim 1, wherein at least one of the antenna pattern, the first electrode, the second electrode, and the circuit wiring includes:
solid particles of at least one selected from silver (Ag), copper (Cu), and aluminum (Al) each having a spherical or flake shape; and
organic matters of at least one selected from polyethylene oxide (PEO) series, oleic acid series, acrylate series, acetate series, and epoxy series.

11. The sensor of claim 1, wherein at least one of the antenna pattern, the first electrode, the second electrode, and the circuit wiring has pores.

12. The sensor of claim 1, wherein the substrate comprises:
a soft plastic layer; and
a silica layer formed between the plastic layer and the antenna pattern, the first electrode, the second electrode, and the circuit wiring.

13. The sensor of claim 1, wherein a line width of the antenna pattern is from 500 μm to 1,500 μm, and a spacing between lines of the antenna pattern is from 300 μm to 700 μm.

14. The sensor of claim 1, wherein the antenna pattern, the sensing electrode, and the circuit wiring are formed of powder ink or paste, and
wherein the powder ink or the paste is composed of:
solid particles of at least one selected from silver (Ag), copper (Cu), and aluminum (Al) for 40 to 70 weight percent; and organic matters of at least one selected from polyethylene oxide (PEO) series, oleic acid series, acrylate series, acetate series, and epoxy series for 30 to 60 weight percent.

15. The sensor of claim 14, wherein the powder ink or the paste is composed of solvent of at least one selected from a group consisting of acetone, allyl alcohol, acetic acid, acetol, methylalcohol, and benzene.

16. A sensor, comprising:
a substrate;
an antenna pattern formed in a spiral shape on the substrate and configured to receive a radio signal from an external device so as to transmit a digital signal to the external device;
a first electrode and a second electrode formed on the substrate and spaced apart from each other in parallel and configured to sense a measurement value representing a change in inputted alternating current power corresponding to a change in impedance by a sensing target material being brought into contact therewith;
a circuit wiring formed to be connected to each of the first electrode and the second electrode;
a circuit insulating layer disposed on at least a portion of the circuit wiring and having a window to expose the first electrode and the second electrode; and
an element bonded to the antenna pattern and the circuit wiring,
wherein the antenna pattern, the first electrode, the second electrode, and the circuit wiring are formed of a same material and form a same layer, and
wherein the element generates the alternating current power with the radio signal to supply the alternating current power to the first electrode and the second electrode through the circuit wiring, and generates the digital signal corresponding to the measurement value to transmit the digital signal to the external device through the antenna pattern.

17. A sensor, comprising:
a substrate;
an antenna pattern formed in a spiral shape on the substrate and configured to receive a radio signal from an external device so as to transmit a digital signal to the external device;
a first electrode and a second electrode formed on the substrate and spaced apart from each other in parallel and configured to sense a measurement value representing a change in inputted alternating current power corresponding to a change in impedance by a sensing target material being brought into contact therewith;
a circuit wiring formed to be connected to each of the first electrode and the second electrode; and
an element bonded to the antenna pattern and the circuit wiring,
wherein the element comprises:
a communicator receiving the radio signal from the antenna pattern and supplying the digital signal to be transmitted through the antenna pattern;
a power generator generating direct current power with the radio signal; and
a controller woken up by the direct current power to convert the direct current power into alternating current power so as to supply the alternating current power to the first electrode and the second electrode, and when the sensing target material is brought into contact therewith to thereby supply the digital signal to the communicator, generating the digital signal corresponding to at least one of ion concentration representing water quality of the sensing target material or salinity of the sensing target material according to a measurement voltage corresponding to an impedance change between the first electrode and the second electrode,
wherein when the radio signal is a signal requesting measurement of the ion concentration, the controller controls the power generator so that a first driving current set by the direct current power is supplied to the first electrode and the second electrode, and when the measurement voltage satisfies a set first ion reference voltage, the controller generates the digital signal corresponding to the ion concentration calculated by applying the measurement voltage to a set first logarithmic function, and
when the measurement voltage does not satisfy the first ion reference voltage, the controller controls the power generator so that a second driving current lower than the first driving current set by the direct current power is supplied to the first electrode and the second electrode, and when the measurement voltage satisfies a second ion reference voltage, the controller generates the digital signal corresponding to the ion concentration calculated by applying the set measurement voltage to a second logarithmic function that is different from the first logarithmic function.

18. The sensor of claim 17, wherein,
when the measurement voltage for the second driving current does not satisfy the second ion reference voltage, the controller generates the digital signal corresponding to the ion concentration calculated by applying the measurement voltage to a set primary single equation.

19. The sensor of claim 17, wherein,
when the radio signal is a signal requesting measurement of salinity, the controller controls the power generator so that driving voltage set by the direct current power is supplied to the first electrode and the second electrode, and when a sampling voltage obtained by sampling the measurement voltage according to a set sampling cycle falls within a range of a second sampling voltage value greater than a range of a set first sampling voltage value after a predetermined time has passed, the controller generates the digital signal corresponding to salinity calculated by applying the sampling voltage to a set primary single equation.

20. The sensor of claim 19, wherein,
when the sampling voltage falls within the range of the first sampling voltage value, the controller controls the power generator so that the driving voltage is re-supplied to the first electrode and the second electrode, and when the sampling voltage obtained by sampling the measurement voltage according to the sampling cycle falls within the range of the first sampling voltage value, the controller generates the digital signal corresponding to salinity calculated by applying the sampling voltage to a set third logarithmic function.

21. The sensor of claim 20, wherein,
when the sampling voltage does not fall within the range of the first sampling voltage value, the controller determines that the sampling voltage falls within the range of the second sampling voltage value and generates the digital signal corresponding to salinity calculated by applying the sampling voltage to the primary single equation.

22. The sensor of claim 17, wherein,
when the radio signal is a signal requesting measurement of the salinity and including temperature of the sensing target material, the controller controls the power generator so that driving voltage set by the direct current power is supplied to the first electrode and the second electrode, and when the temperature of the sensing target material falls within a first temperature range and a sampling voltage obtained by sampling the measurement voltage according to a set sampling cycle falls within a range of a second temperature sampling voltage value greater than a range of a first temperature sampling voltage value, the controller generates the digital signal corresponding to salinity calculated by applying the sampling voltage to a set primary single equation.

23. The sensor of claim 22, wherein,
when the sampling voltage falls within the range of the first temperature sampling voltage value, the controller controls the power generator so that the driving voltage is re-supplied to the first electrode and the second electrode, and when the sampling voltage obtained by sampling the measurement voltage according to the sampling cycle falls within the range of the first temperature sampling voltage value, the controller generates the digital signal corresponding to salinity calculated by applying the sampling voltage to a set fourth logarithmic function.

24. The sensor of claim 23, wherein,
when the sampling voltage does not fall within the range of the first temperature sampling voltage value, the controller determines that the sampling voltage falls within the range of the second temperature sampling voltage value and generates the digital signal corresponding to salinity calculated by applying the sampling voltage to the primary single equation.

25. The sensor of claim 17, wherein,
when the radio signal is a signal requesting measurement of the salinity and including temperature of the sensing target material, the controller controls the power generator so that driving voltage set by the direct current power is supplied to the first electrode and the second electrode, and when the temperature of the sensing target material falls within a range of a second temperature and a sampling voltage obtained by sampling the measurement voltage according to a set sampling cycle falls within a range of a fourth temperature sampling voltage value greater than a range of a third temperature sampling voltage value, the controller generates the digital signal corresponding to salinity calculated by applying the sampling voltage to a set fifth logarithmic function.

26. The sensor of claim 25, wherein,
when the sampling voltage falls within the range of the third temperature sampling voltage value, the controller controls the power generator so that the driving voltage is re-supplied to the first electrode and the second electrode, and when the sampling voltage obtained by sampling the measurement voltage according to the sampling cycle falls within the range of the third temperature sampling voltage value, the controller generates the digital signal corresponding to salinity calculated by applying the sampling voltage to a set sixth logarithmic function.

27. The sensor of claim 26, wherein,
when the sampling voltage does not fall within the range of the third temperature sampling voltage value, the controller determines that the sampling voltage falls within the range of the fourth temperature sampling voltage value and generates the digital signal corresponding to salinity calculated by applying the sampling voltage to a seventh logarithmic function.

28. The sensor of claim 17, wherein the measurement voltage is from 0.1 V to 4 V.

29. A method for operating a sensor, the method comprising:
generating direct current power with a radio signal by receiving the radio signal from an external device;
determining whether the radio signal is a signal requesting measurement of the ion concentration representing water quality of a sensing target material or a signal requesting measurement of salinity of the sensing target material, by being woken up by the direct current power;
supplying a first driving current to a first electrode and a second electrode to sense a first measurement voltage corresponding to an impedance change of the first electrode and the second electrode to which the sensing target material is brought into contact with when the radio signal is determined to be the signal requesting the measurement of ion concentration;
determining whether the first measurement voltage satisfies a set ion reference voltage;
transmitting a first digital signal corresponding to the ion concentration calculated by applying the first measurement voltage to a set first logarithmic function to the external device when the first measurement voltage satisfies the ion reference voltage;
supplying a second driving current lower than the first driving current to the first electrode and the second electrode, when the first measurement voltage does not satisfy the ion reference voltage;
determining whether a second measurement voltage sensed at the first electrode and the second electrode by the second driving current satisfies the ion reference voltage; and
transmitting a second digital signal corresponding to the ion concentration calculated by applying the second measurement voltage to a set second logarithmic function to the external device, when the second measurement voltage satisfies the ion reference voltage.

30. The method of claim 29, further comprising:
when the second measurement voltage does not satisfy the ion reference voltage, generating a third digital signal corresponding to the ion concentration calculated by applying the second measurement voltage to a set primary single equation so as to transmit the third digital signal to the external device.

31. The method of claim 29, further comprising:
when the radio signal is determined to be the signal requesting measurement of salinity,
supplying driving voltage to the first electrode and the second electrode to sense a third measurement voltage corresponding to the impedance change of the first electrode and the second electrode to which the sensing target material is brought into contact with;
determining whether a predetermined time has passed after the driving voltage is supplied;
receiving the third measurement voltage sensed at the first electrode and the second electrode when the predetermined time has passed;
determining whether the first sampling voltage obtained by sampling the third measurement voltage according to a set sampling cycle falls within either a range of a set first sampling voltage value or a range of a second sampling voltage value greater than the first sampling voltage value; and when the first sampling voltage falls within the range of the second sampling voltage value, generating a fourth digital signal corresponding to salinity calculated by applying the first sampling voltage to a set primary single equation so as to transmit the fourth digital signal to the external device.

32. The method of claim 31, further comprising:

when the first sampling voltage falls within the range of the first sampling voltage value, re-supplying the driving voltage to the first electrode and the second electrode and receiving a fourth measurement voltage sensed at the first electrode and the second electrode;

determining whether the second sampling voltage obtained by sampling the fourth measurement voltage according to the sampling cycle falls within the range of the first sampling voltage value; and when the second sampling voltage falls within the range of the first sampling voltage value, generating a fifth digital signal corresponding to salinity calculated by applying the second sampling voltage to a set third logarithmic function so as to transmit the fifth digital signal to the external device.

33. The method of claim 32, further comprising:

when the second sampling voltage does not fall within the range of the first sampling voltage value, determining that the second sampling voltage falls within the range of the second sampling voltage value and generating a sixth digital signal corresponding to salinity calculated by applying the second sampling voltage to the primary single equation so as to transmit the sixth digital signal to the external device.

34. The method of claim 29, further comprising:

when the radio signal is confirmed to be a signal requesting measurement of the salinity and including temperature of the sensing target material in the determining whether the radio signal is the signal requesting measurement, determining whether the temperature of the sensing target material falls within either a first temperature range or a second temperature range;

supplying driving voltage to the first electrode and the second electrode to sense a fifth measurement voltage corresponding to the impedance change of the first electrode and the second electrode to which the sensing target material is brought into contact with when the temperature of the sensing target material falls within the first temperature range;

receiving the fifth measurement voltage sensed at the first electrode and the second electrode;

determining whether a third sampling voltage obtained by sampling the fifth measurement voltage according to a set sampling cycle falls within either a range of a set first temperature sampling voltage value or a range of a second temperature sampling voltage value greater than the first temperature sampling voltage value; and when the third sampling voltage falls within the range of the second temperature sampling voltage value, generating a seventh digital signal corresponding to salinity calculated by applying the third sampling voltage to a set primary single equation so as to transmit the seventh digital signal to the external device.

35. The method of claim 34, further comprising:

when the third sampling voltage falls within the range of the first temperature sampling voltage value, re-supplying the driving voltage to the first electrode and the second electrode and receiving a sixth measurement voltage sensed at the first electrode and the second electrode;

determining whether a fourth sampling voltage obtained by sampling the sixth measurement voltage according to the sampling cycle falls within the range of the first temperature sampling voltage value; and when the fourth sampling voltage falls within the range of the first temperature sampling voltage value, generating an eighth digital signal corresponding to salinity calculated by applying the fourth sampling voltage to a set fourth logarithmic function so as to transmit the eighth digital signal to an external device.

36. The method of claim 35, further comprising:

when the fourth sampling voltage does not fall within the range of the first temperature sampling voltage value, determining that the fourth sampling voltage falls within the range of the second temperature sampling voltage value and generating a ninth digital signal corresponding to salinity calculated by applying the fourth sampling voltage to a set primary single equation so as to transmit the ninth digital signal to the external device.

37. The method of claim 34, further comprising:

when the temperature of the sensing target material falls within the second temperature range, supplying the driving voltage to the first electrode and the second electrode to sense a seventh measurement voltage corresponding to the impedance change of the first electrode and the second electrode to which the sensing target material is brought into contact with;

receiving the seventh measurement voltage sensed at the first electrode and the second electrode;

determining whether a fifth sampling voltage obtained by sampling the seventh measurement voltage according to a sampling cycle falls within either a range of a set third temperature sampling voltage value or a range of a fourth temperature sampling voltage value greater than the third temperature sampling voltage value; and when the fifth sampling voltage falls within the range of the fourth temperature sampling voltage value, generating a tenth digital signal corresponding to salinity calculated by applying the fifth sampling voltage to a set fifth logarithmic function so as to transmit the tenth digital signal to the external device.

38. The method of claim 37, further comprising:

when the fifth sampling voltage falls within the range of the third temperature sampling voltage value, re-supplying the driving voltage to the first electrode and the second electrode and receiving an eighth measurement voltage sensed at the first electrode and the second electrode;

determining whether a sixth sampling voltage obtained by sampling the eighth measurement voltage according to the sampling cycle falls within the range of the third temperature sampling voltage value; and when the sixth sampling voltage falls within the range of the third temperature sampling voltage value, generating an eleventh digital signal corresponding to salinity calculated by applying the sixth sampling voltage to a set sixth logarithmic function so as to transmit the eleventh digital signal to the external device.

39. The method of claim 38, further comprising:
when the sixth sampling voltage does not fall within the range of the third temperature sampling voltage value, determining that the sixth sampling voltage falls within the range of the fourth temperature sampling voltage value to generate a twelfth digital signal corresponding to salinity calculated by applying the sixth sampling voltage to the fifth logarithmic function.

* * * * *